(12) United States Patent
Tchistiakova et al.

(10) Patent No.: US 7,112,654 B2
(45) Date of Patent: *Sep. 26, 2006

(54) LIGAND FOR VASCULAR ENDOTHELIAL GROWTH FACTOR RECEPTOR

(75) Inventors: Lioudmila Tchistiakova, Laval (CA); Shengmin Li, Laval (CA); Grzegorz Pietrzynski, Montreal (CA); Valery Alakhov, Baie d'Urfe (CA)

(73) Assignee: Supratek Pharma Inc., (CA)

( * ) Notice: Subject to any disclaimer, the term of this patent is extended or adjusted under 35 U.S.C. 154(b) by 187 days.

This patent is subject to a terminal disclaimer.

(21) Appl. No.: 10/784,589

(22) Filed: Feb. 23, 2004

(65) Prior Publication Data

US 2004/0266694 A1    Dec. 30, 2004

Related U.S. Application Data

(63) Continuation of application No. 09/775,743, filed on Feb. 2, 2001, now Pat. No. 6,733,755.

(51) Int. Cl.
| | |
|---|---|
| *A61K 38/04* | (2006.01) |
| *C07K 7/00* | (2006.01) |
| *A61K 47/00* | (2006.01) |
| *C07K 5/00* | (2006.01) |
| *C07K 4/00* | (2006.01) |
| *C07K 17/00* | (2006.01) |
| *C07K 9/00* | (2006.01) |

(52) U.S. Cl. .............. 530/327; 530/322; 530/323; 530/333

(58) Field of Classification Search .............. None
See application file for complete search history.

(56) References Cited

U.S. PATENT DOCUMENTS 6,380,370 B1 * 4/2002 Doucette-Stamm et al. .................. 536/23.1

6,733,755 B1 * 5/2004 Tchistiakova et al. ... 424/185.1

FOREIGN PATENT DOCUMENTS

| EP | 0 882 799 | 12/1998 |
| EP | 1 086 956 | 3/2001 |
| WO | WO 89/01493 | 2/1989 |
| WO | WO 95/21868 | 8/1995 |
| WO | WO 00/55206 | 9/2000 |
| WO | WO 01/09157 | 2/2001 |

OTHER PUBLICATIONS

Roselilde et al.. APMIS. 2004. 112: 481-95.*
Iniguez et al. Trends in Mol. Med. 2003. 9:73-78.*
Ecklin, D.J., et al., "Monoclonal Anti-Vascular Endothelial Growth Factor (VEGF) Receptor (KDR) Antibodies Which are Inhibitors of VEGF Binding and Antagonists of VEGF-Stimulated Signaling and Growth of Human Endothelial Cells", AACR, 39:96 (Mar. 1998).
Iro, Nobuyuki, Journal of Biological Chemistry, 273:23410-23418 (1998).

* cited by examiner

*Primary Examiner*—Janet L. Andres
*Assistant Examiner*—Chang-Yu Wang
(74) *Attorney, Agent, or Firm*—Gibbons, Del Deo, Dolan, Griffinger & Vecchione

(57) ABSTRACT

The present invention relates to compositions comprised of a peptide ligand or derivatives thereof that are capable of specific binding to the high affinity receptor-1 of vascular endothelial growth factor (VEGF) and structure similar receptors. The invention further provides a peptide ligand or derivatives thereof that are capable of inhibiting angiogenesis induced by VEGF. The present invention also provides a method for treatment or diagnosis of disease associated with angiogenesis in a patient in need of therapy comprising administering to the patient an effective amount of the pharmaceutical composition of the present invention and a pharmaceutical acceptable carrier.

6 Claims, No Drawings

LIGAND FOR VASCULAR ENDOTHELIAL GROWTH FACTOR RECEPTOR

CROSS REFERENCE TO RELATED APPLICATIONS

This application is a continuation of U.S. Ser. No. 09/775,743, filed on Feb. 2, 2001 now U.S. Pat. No. 6,733,755.

FIELD OF THE INVENTION

The present invention relates to compositions comprised of a peptide ligand or derivatives thereof (hereinafter, "Ligand") that are capable of specifically binding to the high affinity receptor-1 of vascular endothelial growth factor (hereinafter, "VEGF") and structure similar receptors. The invention further describes the Ligand that is capable of inhibiting angiogenesis induced by VEGF. The invention further describes compositions comprised of a Ligand, or its complex with a carrier associated with a biological agent. The invention further relates to a method of inhibiting angiogenesis by using a Ligand or its complex with a carrier alone or associated with a biological agent. The invention further relates to a method for targeting of a biological agent to a predetermined compartment by associating the agent with a Ligand or its complex with a carrier. These compositions are well suited for use as therapeutic and diagnostic agents for the pathologies that are associated with an increased level of VEGF receptors, and as vehicles for delivering biologically active and diagnostic agents to the sites in which VEGF receptor levels are increased.

BACKGROUND OF THE INVENTION

The growth of new blood vessels from existing endothelium (angiogenesis) is tightly controlled in healthy adults by opposing effects of positive and negative regulations. Under certain pathological conditions, including proliferative retinopathies, rheumatiod arthritis, psoriasis and cancer, positive regulations prevail and angiogenesis contributes to disease progression (Folkman (1995) *Nature Medicine* 1:27–31; Achen and Stacker (1998) *Int. J. Exp. Pathol.* 79:255–265). In cancer, the notion that angiogenesis represents the rate limiting step of tumor growth and metastasis, (Folkman (1971) *New Engl. J. Med.* 285:1182–1186) is now supported by considerable experimental evidence (reviewed in Aznavoorian et al. (1993) *Cancer* 71:1368–1383; Bidfer and Ellis (1994) *Cell* 79:185–188; Plate and Warnke (1997) *J. Neurooncol* 35:365–372; de Jong et al. (1998) *J. Pathol* 184:44–52).

A number of angiogenic growth factors have been described to date among which vascular endothelial growth factor (VEGF) appears to play a key role in the regulation of vasculogenesis and angiogenesis as a highly specific mitogen for endothelial cells (Brown et al., (1997) *Control of Angiogenesis* (Goldberg and Rosen, eds) Birkhauser, Basel, pp 233–269; Martiny-Broun and Marme(1995) *Current Opin. in Biotech.* 6:675–680; Ferrara and Davis-Smyth (1997) *Endocrine Reviews* 18:4–25).

VEGF is a glycosylated, disulfide-linked homodimeric protein consisting of two 23 kD subunits. Four different monomeric isoforms of VEGF exist ranging in size from 121 to 206 residues in humans ($VEGF_{121}$, $VEGF_{165}$, $VEGF_{189}$ and $VEGF_{206}$). Transcripts encoding the three shorter forms are detected in the majority of tumor cells and tumor tissue expressing VEGF gene. The isoforms result from different splicing events, and all variants share the same 115 N-terminal as well as six C-terminal residues and have a leader sequence to leave the cells. $VEGF_{165}$ is the dominant isoform, while $VEGF_{206}$ has so far only been identified in human fetal liver cDNA library $VEGF_{165}$ and $VEGF_{189}$ bind heparin with high affinity, and are sequestered to the cell surface or within the extracellular matrix bound to proteoglycans, while $VEGF_{121}$ does not bind heparin and is thus freely diffusible. Plasmin cleavage of $VEGF_{165}$ generates a 110-residue long N-terminal fragment (the receptor-binding domain) that no longer binds heparin but is equipotent to VEGF121 in its ability to induce endothelial cell proliferation.

VEGF is expressed in embryonic tissues (Breier et al., (1992) *Development* (Camb.) 114:521), macrophages, proliferating epidermal keratinocytes during wound healing (Brown et al., (1992) *J. Ex. Med.* 176:1375–9) and may be responsible for tissue edema associated with inflammation (Ferrara and Davis-Smyth (1997) *Endocrine Reviews* 18:4–25). In situ hybridization studies have demonstrated high VEGF expression in a number of human tumors including glioblastoma, ovarian tumors, carcinoma, hemangioblastoma, brain neoplasms and Kaposi's sarcoma (Plate et al., (1992) *Nature* 359:845–848; Zebrowski et al., (1999) *Ann. Surg. Oncol.* 6:373–378). High levels of VEGF were also observed in hypoxia-induced angiogenesis (Shweiki et al., (1992) *Nature* 359:843–845).

The biological function of VEGF is mediated through binding to two high affinity receptors which are selectively expressed on endothelial cells during embryogenesis (Millauer et al., (1993) *Cell* 72:835–838) and VEGF related pathologies (tumor formation). VEGF receptors include the human kinase domain receptor (KDR), described in U.S. Pat. No. 5,712,380; its murine analog flk-1, sequenced by Mallhews (1991) *Proc. Natl. Acad. Sci. USA*, 88:9026–9030; U.S. Pat. No. 5,270,458 and the Fsm-like tyrosine kinase (Flt-1) (Shibuya et al., (1990) *Oncogene* 5:519–524). All of them are class III tyrosine kinases (Vaisman et al., 1990: *J. Biol. Chem.* 265, 19461–19466; Kaipainen et al., (1993) *J. Exp. Med.* 178:2077–2088). Studies in mice have shown that the expression of KDR reaches the highest levels during embryonic vasculogenesis and angiogenesis (Millauer et al., 1993 *Cell* 72:835–838). In contrast, only low levels of mRNA for Flt-1 were found during fetal growth and moderate levels during organogenesis, but high levels in newborn mice (Peters et al., 1993 *Proc. Natl. Aca. Sci. U.S.A* 90(16):7533–7). Experiments with knockout mice deficient in either receptor revealed that KDR is essential for the development of endothelial cells, whereas Flt-1 is necessary for the organization of embryonic vasculature (Fong et al., 1995 *Dev. Dyn.* 203(1):80–92; Shalaby et al., 1995 *Nature* 376 (6535:62–6).

KDR and Flt-1, each ~1300 amino acid residues long, are composed of 7 extracellular Ig-like domains containing the ligand-binding region, a single short membrane-spanning sequence, and an intracellular region containing tyrosine kinase domains. The amino acid sequences of KDR and Flt-1 are ~45% identical to each other. Flt-1 has the higher affinity for VEGF ($K_D$=10–20 pM) compared to 75–125 pM for the KDR receptor. VEGF binding to KDR but not Flt-1 elicits an efficient (ED50~0.1–1 ng/ml) DNA synthetic and chemotactic endothelial cell response. Activation of Flt-1 receptor by VEGF might modulate the interaction of endothelial cells with each other or the basement membrane on which they reside.

The Flt-1 receptor mRNA can be spliced to generate forms encoding either the full-length membrane-spanning receptor or a soluble form, denoted sFlt-1. Pure sFlt-1 retains its specific high affinity binding for VEGF and fully inhibits VEGF-stimulated endothelial cell mitogenesis by dominant negative mechanism.

Like other growth factor transmembrane tyrosine kinase receptors, VEGF receptors presumably undergo ligand-induced dimerization, that triggers signal transduction by promoting either autophosphorylation or transphosphorylation specific downstream signal transduction protein mediators.

To gain a better understanding of the biological activity of VEGF the analysis of structure/activity relationships was performed using site-directed mutagenesis and epitope mapping of neutralizing monoclonal antibodies (Keyt et al., (1996) *J. Biol. Chem.* 271:5638–5646). Arg82, Lys84 and His86, located in a hairpin loop, were found to be critical for binding KDR/Flk-1, while negatively charged residues, Asp63, Glu64 and Glu67, were associated with Flt-1 binding. The three-dimensional structure of the receptor-binding domain of VEGF (residues 8–109) showed that these positively and negatively charged regions are distal in the monomer but are spatially close in the dimer (Wiesmann et al., (1997) *Cell* 91:695–704). Mutations within the KDR site had minimal effect on Fit-1 binding, suggesting that receptors have different binding sites on VEGF which may serve to dimerize tyrosine kinase receptors resulting in initiation of angiogenesis.

Domain deletion studies on Flt-1 receptor have shown that the ligand binding function resides within the first three domains (Barleon et al., (1997) *J. Biol. Chem.* 272:10382–1038; Cunningham et al., (1997) *Biochim. Biophys. Res. Commun.* 231 (3): 596–599), and domain 4 is required to efficiently couple ligand binding to signal transduction by means of direct receptor-receptor contacts (Barleon et al., (1997) *J. Biol. Chem.* 272:10382–10388). The crystal structure of the complex between VEGF and the second domain of Flt-1 showed domain 2 in a predominantly hydrophobic interaction with the "poles" of VEGF dimer (Wiesmann et al., (1997) *Cell* 91:695–704). Deletion experiments on KDR demonstrated that only domain 2 and 3 are critical for ligand binding (Fuh et al., (1998) *J. Biol Chem.* 1998; 273 (18):11197–204).

Endothelial cells also contain another type of VEGF receptors, Neuropilins (NP), possessing a lower mass than either VEGFR2 or VEGFR1 (Gluzman-Poltorak Z., et al., (2000) *J. Biol. Chem.*, 275(24):18040–5; WO Patent 0002/3565A2). It was subsequently found that these smaller VEGF receptors of endothelial cells are isoform specific receptors that bind VEGF165 but not VEGF121 (Gluzman-Poltorak Z, et al., (2000) *J. Biol. Chem.*, 275(38):29922). Unusually large amounts of these isoform-specific receptors were found in several types of prostate and breast cancer cell lines (Miao, H. Q., et al., (2000) *FASEB J.*, 14(15):2532–9). Neuropilin-1 is likely to play an important role in the development of the cardiovascular system. Gene disruption studies have indicated that np-1 participates in embryonic vasculogenesis and angiogenesis and is involved in the maturation of blood vessels, since mouse embryos lacking a functional np-1 gene die because their cardiovascular system fails to develop properly (Kawasaki, T., et al., (1999) *Neurobiol.* 39(4):579–89). Subsequent experiments have shown that NP-1 also serves as a receptor for the heparin-binding form of placenta growth factor (PlGF), PlGF-2, and for VEGF-B.

In addition to its normal physiological role, VEGF receptors are associated with numerous pathologies, including cancer, rheumatiod arthritis, diabetic retinopathy and psoriasis; development of VEGF antagonists, blocking the interaction between VEGF and its receptors with is therefore clinically attractive. Humanized neutralizing antibodies have been shown to interact with VEGF near the KDR and Flt-i binding sites (Kim, K. J., et al., (1993) *Nature* 362, 841–844; Muller, Y. A., et al., (1997) *Proc. Nat. Acad. Sci.* 94, 7192–7197; Muller, Y. A. et al., (1998) *Structure* 6:1153–1167; U.S. Pat. No. 5,855,866), and SELEX-derived RNA molecules (Jellinek, D. et al., (1994) *Biochemistry* 33:10450–10456; U.S. Pat. No. 5,859,228), that target VEGF, suppress tumor growth that is dependent on vascularization of adjacent normal tissue (Plate, K. H. et al., (1994) *Brain-Pathol.*, 4:207–218). Anti KDR monoclonal antibodies inhibited VEGF induced signaling and demonstrated high anti-tumor activity (Witte et al., (1998) *Cancer & Metast. Reviews* 17:155–161; U.S. Pat. No. 5,840,301). Soluble Fit receptor (U.S. Pat. No. 5,861,484), fragments of VEGF (U.S. Pat. No. 5,240,848) have been shown to inhibit factor/receptor interaction and angiogenesis in vivo. Anti VEGF antisense oligonucleotide was designed to inhibit VEGF expression and VEGF induced neovascularization (U.S. Pat. No. 5,641,756).

The present invention describes a new ligand for VEGF receptor-1 and similar receptors with is useful for targeted delivery of therapeutics. Such treatment should be as devoid as possible of undesired side effects such as those associated with conventional chemotherapy and some of the experimental biotherapies.

SUMMARY OF THE INVENTION

The present invention provides a pharmaceutical composition comprising at least one peptide or derivative thereof, wherein said polypeptide or derivative thereof is capable of specific binding with the high affinity VEGF receptor-1 or a derivative of the VEGF receptor-1 and structural similar receptors. Such a polypeptide is herein referred to as Ligand.

In one embodiment, the present invention provides a peptide or derivative thereof that is capable of specific binding with VEGF receptors.

In another embodiment, a pharmaceutical composition of the present invention comprises at least one peptide or derivative thereof, wherein said peptide or derivative thereof is capable of specific binding with the high affinity VEGF receptor-1 or a derivative of the VEGF receptor-1 and structural similar receptors. Such a composition may further comprise the ability to modulate the interaction of VEGF with its high affinity VEGF receptor and modulates biological effects mediated by binding.

A preferred peptide of the present invention provides the amino acid sequence of Asn-Gly-Tyr-Glu-Ile-Glu-Trp-Tyr-Ser-Trp-Val-Thr-His-Gly-Met -Tyr (SEQ ID NO: 1) wherein the peptide is a ligand of VEGF receptor-1 and inhibits binding of VEGF to this receptor.

The present further provides a pharmaceutical composition, wherein the polypeptide or derivative thereof comprise the amino acid sequence of SEQ ID NOs: 1; 2; 3; 4; 5; or 7.

A preferred peptide, variant or derivative of peptide of the present invention has the sequence Asn-X-X-Glu-Ile-Glu-X-X-X-Trp-X-X-X-X-X-Tyr (SEQ ID NO: 7) (also abbreviated in single letter amino acid code as NXXEIEXXX-WXXXXXY), where X is any amino acid.

Another embodiment of the present invention provides at least one peptide compound having the motif of SEQ ID NO: 8:

$Y_1$-X-X-$Y_2$-$Y_3$-$Y_4$-X-X-X-$Y_5$-X-X-X-X-X-$Y_6$, where $Y_1$ is Asn or Gln $Y_2$ is negatively charged amino acid comprising of Glu or Asp
$Y_3$ is Ile, Leu, Val or Met
$Y_4$ is negatively charged amino acid comprising of Glu or Asp
$Y_5$ is aromatic amino acid comprising of Trp, Phe, Tyr or His
$Y_6$ is aromatic amino acid comprising of Tyr, Trp, Phe or His
X is any amino acid,
or a substitution variant, addition variant or other chemical derivative thereof.

The present invention also provides analogs of the pharmaceutical composition which can comprise in its molecular structure residues being derivatives of compounds other than amino acids, referenced herein as "peptide mimetics" or "peptidomimetics". Other analogs of peptide Ligand are compounds having changed topology of its chain, in particular nonlinear compounds, which have chemical bonds that close cycle or cycles in the molecule and constrain its structure.

The peptide Ligand of the present invention can be made by using well-known methods including recombinant methods and chemical synthesis. Recombinant methods of producing a peptide through the introduction of a vector including nucleic acid encoding the peptide into a suitable host cell is well known in the art, such as is described in Sambrook et al., Molecular Cloning: A Laboratory Manual, 2d Ed, Vols. 1 to 8, Cold Spring Harbor, N.Y. (1989), which is herein incorporated by reference. A linear sequence is synthesized, for example, by the solid phase peptide synthesis of Merrifield et al., *J. Am. Chem. Soc.*, 85:2149 (1964), which is incorporated herein by reference). Alternatively, a peptide of the present invention can be synthesized using standard solution methods well known in the art (see, for example, Bodanszky, M., Principles of Peptide Synthesis (Springer-Verlag, 1984)), which is herein incorporated by reference). Newly synthesized peptides can be purified, for example, by high performance liquid chromatography (HPLC), and can be characterized using, for example, mass spectrometry or amino acid sequence analysis. Although a purity of greater than 95 percent for the synthesized peptide is preferred, lower purity may be acceptable. The analogs of the peptide Ligand can be peptides with altered sequence comprising another selection of L-α-amino acid residues, D-α-amino acid residues, non-α-amino acid residues.

Therefore, in another embodiment, the pharmaceutical composition of the present invention provides that derivatives of SEQ ID NO: 1 comprise of oligopeptides, chemical derivatives or peptidomimetic that are capable of specific binding with the high affinity VEGF receptor-1 or a derivative of the VEGF receptor-1.

In another embodiment of the invention the Ligand is associated with a biological agent. Such an association can be achieved by chemical, genetic or physical linking of the Ligand and the biological agent, or by mixing the above components, or by their co-administration.

The peptide, derivative or peptidomimetic of this invention has one or more of the following activities:

The present invention provides a pharmaceutical composition comprising at least one peptide or derivative thereof, wherein said polypeptide or derivative thereof is capable of specific binding with the high affinity VEGF receptor-1 or a derivative of the VEGF receptor-1 and structural similar receptors wherein the polypeptide or derivative thereof comprises at least about 20% of the biological activity of the polypeptide or derivative thereof SEQ ID NO: 3.

Still further, the present invention provides a pharmaceutical composition comprising at least one peptide or derivative thereof, wherein the polypeptide or derivative thereof is capable of specific binding with the high affinity VEGF receptor-1 or a derivative of the VEGF receptor-1 and structural similar receptors wherein the polypeptide or derivative thereof comprises binding activity such that the polypeptide or derivative thereof competes with the labeled polypeptide in SEQ ID NO: 4 for binding to the VEGF receptor-1.

Yet still further, the present invention provides a pharmaceutical composition comprising at least one peptide or derivative thereof, wherein the polypeptide or derivative thereof is capable of specific binding with the high affinity VEGF receptor-1 or a derivative of the VEGF receptor-1 and structural similar receptors, wherein the polypeptide or derivative thereof comprises at least about 20% of the biological activity of the peptide or derivative thereof SEQ ID NO: 3 and binding activity such that the peptide or derivative thereof competes with the labeled peptide in SEQ ID NO: 4 for binding to the VEGF receptor-1.

The biological activity of the present pharmaceutical composition is measured but is not limited to using in vitro bioassays comprising VEGF receptor-1 binding assay, endothelial tube formation on, MATRIGEL™ extracellular matrix proteins or endothelial cell mitogenic assay.

The invention further includes a pharmaceutical composition comprising one or more Ligands in association with a carrier. In another embodiment of the invention the Ligand is associated with a protein, polymer or any other carrier to improve the ability of the Ligand to interact with VEGF receptor and/or to improve pharmacological properties of the Ligand such as pharmacokinetics, stability and biodistribution. The association of the Ligand and the carrier can be achieved by chemical, genetic or physical linking of the Ligand and the carrier, or by mixing the above components, or by their co-administration.

In another yet embodiment of the invention the Ligand associated with a carrier is further associated with a biological agent which is achieved by chemical, genetic or physical linking of the Ligand—carrier composition described in the previous embodiment of the invention and a biological agent. The invention further provides a pharmaceutical composition comprising one or more Ligands or their complex with a carrier in association with a biological agent.

Moreover, the present invention extends to pharmaceutical compositions for diagnostics and treatment of diseases, where such diseases are associated with angiogenesis.

The invention is further directed to a pharmaceutical composition useful for diagnostics or treatment of angiogenesis associated diseases, comprising (a) any of the above peptides, variants or chemical derivatives including, but not limited to peptidorimetics and (b) a pharmaceutically acceptable carrier or excipient, either chemically conjugated or physically associated with a ligand.

The invention is further directed to a pharmaceutical composition useful for diagnostics or treatment of angiogenesis associated diseases, comprising any of the above peptides, variants or chemical derivatives including a peptidomimetic conjugated chemically or genetically fused to a therapeutic agent.

Also provided is a method for inhibition of VEGF-induced cell proliferation or angiogenesis in a subject having a disease or condition associated with undesired angiogenesis, comprising administering to the subject an effective amount of a pharmaceutical composition as described above.

In yet another embodiment of the invention the Ligand is associated with a modified biological agent, which is achieved by chemical linking of the Ligand to the modified biological agent, such an associate being a pro-drug and revealing no activity of the biological agent. The active biological agent is released from such an associate upon action of chemical or enzymatic reaction in the body.

The present invention also provides a method of treating a disease associated with angiogenesis in a patient in need of such therapy comprising administering to said patient an effective amount of said pharmaceutical composition of claim 1 and a pharmaceutical acceptable carrier.

In any of the foregoing methods, the disease or condition being treated may be primary tumor growth, tumor invasion or metastasis, atherosclerosis, post-balloon angioplasty vascular restenosis, neointima formation following vascular trauma, vascular graft restenosis, fibrosis associated with a chronic inflammatory condition, lung fibrosis, chemotherapy-induced fibrosis, wound healing with scarring and fibrosis, psoriasis, deep venous thrombosis, or another disease or condition in which angiogenesis is involved.

These and other aspects of the present invention will be better appreciated by reference to the following Sequence Listings and Detailed Description.

-continued

Listing of conjugates

| CONJUGATE NO.: | CONJUGATE |
|---|---|
| 4 | PEI-PEG-peptide(SEQ ID NO: 4) |
| 5 | paclitaxel-PEG-peptide(SEQ ID NO: 4) |
| 6 | F127-peptide(SEQ ID NO: 4) |
| 7 | paclitaxel-polyglutamic acid-peptide (SEQ ID NO: 1) |
| 8 | paclitaxel-peptide (SEQ ID NO: 1): |
| 9 | Peptide (SEQ ID NO: 3)Leucyl-doxorubicin |

DETAILED DESCRIPTION OF THE INVENTION

I. The Ligand

The present invention provides a pharmaceutical composition comprising at least one peptide, or derivatives thereof, which is capable of specific binding with VEGF receptors, such a peptide or its derivative referenced herein as a "Ligand". Since the Ligand is capable of specific binding with the receptors, it is also able to modulate VEGF medi- Sequence Listings

| SEQ ID NO: | Sequence |
|---|---|
| 1 | H-Asn-Gly-Tyr-Glu-Ile-Glu-Trp-Tyr-Ser-Trp-Val-Thr-His-Gly-Met-Tyr-NH$_2$ |
| 2 | H-Cys-Asn-Gly-Tyr-Glu-Ile-Glu-Trp-Tyr-Ser-Trp-Val-Thr-His-Gly-Met-Tyr-NH$_2$ |
| 3 | Ac-Cys-Asn-Gly-Tyr-Glu-Ile-Glu-Trp-Tyr-Ser-Trp-Val-Thr-His-Gly-Met-Tyr-NH$_2$ |
| 4 | Fam-Asn-Gly-Tyr-Glu-Ile-Glu-Trp-Tyr-Ser-Trp-Val-Thr-His-Gly-Met-Tyr-NH$_2$ |
| 5 | Fam-Glu-Glu-Glu-Asn-Gly-Tyr-Glu-Ile-Glu-Trp-Tyr-Ser-Trp-Val-Thr-His-Gly-Met-Tyr-NH$_2$ |
| 6 | Fam-Asn-Gly-Tyr-Ile-Glu-Trp-Tyr-Ser-Trp-Val-Thr-His-Gly-Met-Tyr-NH$_2$ |
| 7 | Asn-X-X-Glu-Ile-Glu-X-X-X-Trp-X-X-X-X-X-Tyr |
| 8 | Y$_1$-X-X-Y$_2$-Y$_3$-Y$_4$-X-X-X-Y$_5$-X-X-X-X-X-Y$_6$ |

Abbreviations

Ac—acetyl,
Fam—fluorescein-5-carbonyl,
X—any amino acid,
Y$_1$ is Asn or Gln,
Y$_2$ is negatively charged amino acid comprising of Glu or Asp,
Y$_3$ is Ile, Leu, Val or Met
Y$_4$ is negatively charged amino acid comprising of Glu or Asp
Y$_5$ is aromatic amino acid comprising of Trp, Phe, Tyr or His
Y$_6$ is aromatic amino acid comprising of Tyr, Trp, Phe or His Listing of conjugates

| CONJUGATE NO.: | CONJUGATE |
|---|---|
| 1 | peroxidase-peptide(SEQ ID NO: 4) |
| 2 | PEG 1500-peptide(SEQ ID NO: 4) |
| 3 | polylysine-PEG1500-peptide(SEQ ID NO: 4) | ated angiogenesis in endothelial cells and tissues. Therefore, present invention also provides pharmaceutical compositions in which the Ligand is used as a targeting moiety to improve the delivery of a biological agent used for therapeutic or diagnostic purpose.

In one preferred embodiment, the invention provides a Ligand of VEGF receptors being peptide, or derivative thereof. The preparation of the peptides or derivatives thereof according to the invention is effected by means of one of the known organic chemical methods for peptide synthesis or with the aid of recombinant DNA techniques.

II. Chemical Peptide Synthesis

The organic chemical methods for peptide synthesis are considered to include the coupling of the required amino acids by means of a condensation reaction, either in homogeneous phase or with the aid of a solid phase. The condensation reaction can be carried out as follows:

a) condensation of a compound (amino acid, peptide) with a free carboxyl group and protected other reactive groups with a compound (amino acid, peptide) with a free amino group and protected other reactive groups, in the presence of a condensation agent;

b) condensation of a compound (amino acid, peptide) with an activated carboxyl group and free or protected other reaction groups with a compound (amino acid, peptide) with a free amino group and free or protected other reactive groups.

Activation of the carboxyl group can take place, inter alia, by converting the carboxyl group to an acid halide, azide, anhydride, imidazolide or an activated ester, such as the N-hydroxy-succinimide, N-hydroxy-benzotriazole or p-nitrophenyl ester. The most common methods for the above condensation reactions are: the carbodiimide method, the azide method, the mixed anhydride method and the method using activated esters, such as described in The Peptides, Analysis, Synthesis, Biology Vol. 1–3 (Ed. Gross, E. and Meienhofer, J.) 1979, 1980, 1981 (Academic Press, Inc.). A particularly useful method is Castro type method using benzotriazole-1-yl-oxy-uronium, or -phoshponium esters, eg. PyBOP (benzotriazole-1-yl-oxy-tris-pyrrolidino-phosphonium hexafluorophosphate) (Martinez, J. et al. (1988) *J. Med. Chem.* 28, 1874).

Preparation of suitable peptides according to the invention using the "solid phase" is for instance described in (1963) *J. Amer. Chem. Soc.* 85:2149 and ((1990) *Int. J. Peptide Protein Res.* 35:161–214. The coupling of the amino acids of the peptide to be prepared usually starts from the carboxyl end side. For this method a solid phase is needed on which there are reactive groups or on which such groups can be introduced. This can be, for example, a copolymer of benzene and divinylbenzene with reactive chloromethyl groups, or a polymeric solid phase rendered reactive with hydroxymethyl or amine function.

After synthesis of the desired amino acid sequence, detaching of the peptide from the resin follows, for example, hydrogen fluoride with trifluoromethanesulphonic acid or with methanesulphonic acid dissolved in trifluoroacetic acid. The peptide can also be removed from the carrier by transesterification with a lower alcohol, preferably methanol or ethanol, in which case a lower alkyl ester of the peptide is formed directly. Likewise, splitting with the aid of ammonia gives the amide of a peptide according to the invention.

A particularly suitable solid phase is, for example, the Rink Amide resin (4-(2',4'-Dimethoxyphenyl-Fmoc-aminomethyl) -phenoxy-copolystrene-1% divinylbenzene resin), described by Rink (1987) *Tetrahedron Lett.,* 28:3787. After synthesis, the peptide can be split from the solid phase under mild conditions using trifluoroacetic acid producing a carboxyamide derivative.

The reactive groups, which may not participate in the condensation reaction, are, as stated, effectively protected by groups, which can be removed again very easily by hydrolysis with the aid of acid, base or reduction. Thus, a carboxyl group can be effectively protected by, for example, esterification with methanol, ethanol, tertiary butanol, benzyl alcohol or p-nitrobenzyl alcohol and amines linked to solid support.

Groups which can effectively protect an amino group are the ethoxycarbonyl, benzyloxycarbonyl, t-butoxy-carbonyl (t-boc) or p-methoxy-benzyloxycarbonyl group, or an acid group derived from a sulphonic acid, such as the benzenesulphonyl or p-toluenesulphonyl group, but other groups can also be used, such as substituted or unsubstituted aryl or aralkyl groups, for example benzyl and triphenylmethyl, or groups such as orthonitrophenyl-sulphenyl and 2-benzoyl-1-methyl-vinyl. A particularly suitable α-amino-protective group is, for example, the base-sensitive 9-fluorenyl-methoxycarbonyl (Fmoc) group (Carpino & Han (1970) *J. Amer. Chem. Soc.* 92, 5748). A more extensive account of possible protecting groups can be found in The Peptides, Analysis, Synthesis, Biology, Vol.1–9 (Eds. Gross, Udenfriend and Meienhofer) 1979–1987 (Academic Press, Inc.).

It is necessary also to protect the ε-amino group of lysine and advisable for the guanidine group of arginine. Customary protective groups in this connection are a Boc group for lysine and a Pmc, Pms, Mbs, or Mtr group for arginine. The protective groups can be split off by various conventional methods, depending on the nature of the particular group, for example with the aid of trifluoroacetic acid or by mild reduction, for example with hydrogen and a catalyst, such as palladium, or with HBr in glacial acetic acid.

III. Biosynthetically Made Peptide

The peptides of the present invention are prepared by any technique, including by well-known recombinant methods. The above techniques are more fully described in laboratory manuals such as "Molecular Cloning: A Laboratory Manual", Second Edition by Sambrook et al., Cold Spring Harbor Press, 1989; "Current Protocols in Molecular Biology", Volumes I–III, Ausubel, R. M., ed., 1994; "Cell Biology: A Laboratory Handbook", Volumes I–III, J. E. Celis, ed., 1994; "Current Protocols in Immunology", Volumes I–III, Coligan, J. E., ed., 1994; "Oligonucleotide Synthesis", M. J. Gait ed., 1984; "Nucleic Acid Hybridization", B. D. Hames & S. J. Higgins eds., 1985; "Transcription And Translation", B. D. Hames & S. J. Higgins, eds., 1984; "Animal Cell Culture", R. I. Freshney, ed., 1986; "Immnobilized Cells And Enzymes", IRL Press, 1986; B. Perbal, "A Practical Guide To Molecular Cloning", 1984.

DNAs encoding the peptides of the invention can be prepared by a variety of methods known in the art. These methods include, but are not limited to, chemical synthesis by any of the methods described in Engels et al., (1989) *Agnew. Chem. Int. Ed. Engl.,* 28:716–734, the entire disclosure of which is incorporated herein by reference, such as the triester, phosphite, phosphoramidite and H-phosphonate methods. In one embodiment, codons preferred by the expression host cell are used in the design of the ligand encoding DNA.

One example of a method of producing the ligand peptide using recombinant DNA techniques entails the steps of (1) synthetically generating DNA oligonucleotide encoding peptide sequence, appropriated linkers and restriction sites coding sequences (2) inserting the DNA into an appropriate vector such as an expression vector, (3) inserting the gene containing vector into a microorganism or other expression system capable of expressing the inhibitor gene, and (7) isolating the recombinantly produced peptides.

Those skilled in the art will recognize that the peptides of the present invention may also be expressed in various cell systems, both prokaryotic and eukaryotic, all of which are within the scope of the present invention. The appropriate vectors include viral, bacterial and eukaryotic expression vectors. A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. The precise nature of the regulatory regions needed for gene sequence expression may vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

For example, the entire coding sequence of the ligand peptide may be combined with one or more of the following in an appropriate expression vector to allow for such expression: (1) an exogenous promoter sequence (2) a ribosome binding site (3) carrier protein (4) a polyadenylation signal (4) a secretion signal. Modifications can be made in the 5'-untranslated and 3'-untranslated sequences to improve expression in a prokaryotic or eukaryotic cell; or codons may be modified such that while they encode an identical amino acid, that codon may be a preferred codon in the chosen expression system. The use of such preferred codons is described in, for example, Grantham et al., (1981) *Nuc. Acids Res.*, 9:43–74 and Lathe, (1985) *J. Mol. Biol.*, 183:1–12, hereby incorporated by reference herein in their entirety. Moreover, once cloned into an appropriate vector, the DNA can be altered in numerous ways as described above to produce functionally equivalent variants thereof.

In another embodiment, the peptide of present invention can be expressed as fusion proteins in which the peptides of invention are fused at its N-terminus or its C-terminus, or at both termini, to one or more of peptide copies. In a preferred embodiment, the fusion protein is specifically cleavable such that at least a substantial portion of the peptide sequence can be proteolytically cleaved away from the fusion protein to yield the desired polypeptide. The fusion proteins of the invention can be designed with cleavage sites recognized by chemical or enzymatic proteases. In one embodiment, the fusion protein is designed with a unique cleavage site (or sites) for removal of the ligand peptide sequence, i.e. the fusion protein is designed such that a given protease (or proteases) cleaves away the ligand peptide sequence but does not cleave at any site within the sequence of the desired protein, avoiding fragmentation of the desired protein. In another embodiment, the cleavage site (or sites) at the fusion joint (or joints) is designed such that cleavage of the fusion protein with a given enzyme liberates the authentic, intact sequence of the desired protein from the remainder of the fusion protein sequence. The pTrcHisA vector (Invitrogen) and other like one can be used to obtain high-level, regulated transcription from the trc promoter for enhanced translation efficiency of fusion protein in *E. coli*. The peptides of invention can be expressed fused to an N-terminal nickel-binding poly-histidine tail for one-step purification using metal affinity resins. The enterokinase cleavage recognition site in the fusion protein allows for subsequent removal of the N-terminal histidine fusion protein from the purified recombinant protein. The ligand fusion protein can be produced using appropriated carrier protein, for example, β-galactosidase, green fluorescent protein, luciferase, dehydrofolate reductase, thireodoxin, protein A Staphylococcus aureus and glutathione S-transferase. These examples are, of course, intended to be illustrative rather than limiting.

The peptides of present invention can be synthesized as a fusion protein with a virus coat protein and expressed on the surface of virus particle, for example bacteriophage M13, T7, T4 and lambda (λ), λgt10, λgt11 and the like; adenovirus, retrovirus and pMAM-neo, pKRC and the like.

In general, prokaryote expression vectors contain replication and control sequences, which are derived from species compatible with the host cell. The vector ordinarily carries a replication site, as well as sequences that encode proteins capable of providing phenotypic selection in transformed cells. For example, vectors include pBR322 (ATCC No. 37,017), phGH107 (ATCC No. 40,011), pBO475, pS0132, pRIT5, any vector in the pRIT20 or pRIT30 series (Nilsson and Abrahmsen, Meth. Enzymol., 185: 144–161 (1990)), pRIT2T, pKK233-2, pDR540, pPL-lambda, pQE70, pQE60, pQE-9 (Qiagen), pBS, phagescript, psiX174, pBluescript SK, pBsKS, pNH8a, pNH16a, pNH18a, pNH46a (Stratagene); pTRC99A, pKK223-3, pKK233-3, pDR540, pRIT5 (Pharmacia). Eukaryotic: pWL-neo, pSV2cat, pOG44, pXT1, pSG (Stratagene) pSVK3, PBPV, pMSG, pSVL (Pharmacia) are suitable for expression in prokaryotic hosts. Such plasmids are, for example, disclosed by Sambrook (cf. "Molecular Cloning: A Laboratory Manual", second edition, edited by Sambrook, Fritsch, & Maniatis, Cold Spring Harbor Laboratory, (1989)). Bacillus plasmids include pC194, pC221, pT127, and the like. Such plasmids are disclosed by Gryczan (In: The Molecular Biology of the Bacilli, Academic Press, NY (1982), pp. 307–329). Suitable *Streptomyces* plasmids include plJ101 (Kendall et al., (1987) *J. Bacteriol.* 169:4177–4183, and *streptomyces* bacteriophages such as .phi.C31 (Chater et al., In: Sixth International Symposium on Actinomycetales Biology, Akademiai Kaido, Budapest, Hungary (1986), pp. 45–54). *Pseudomonas* plasmids are reviewed by John et al. ((1986) *Rev. Infect. Dis.* 8:693–704), and Izaki ((1978) *Jpn. J. Bacteriol.* 33:729–742).

Prokaryotic host cells containing the expression vectors of the present invention include *E. coli* K12 strain 294 (ATCC NO. 31446), *E coli* strain JM101 (Messing et al., *Nucl. Acid Res.*, 9: 309 (1981)), *E. coli* strain B, *E. coli* strain .sub.chi. 1776 (ATCC No. 31537), *E. coli* c600 (Appleyard, (1954) *Genetics*, 39: 440), *E. coli* W3110 (F-, gamma-, prototrophic, ATCC No. 27325), *E. coli* strain 27C7 (W3110, tonA, phoA E15, (argF-lac)169, ptr3, degP41, ompT, kan-.sup.r) (U.S. Pat. No. 5,288,931, ATCC No. 55,244), *Bacillus subtilis, Salmonella typhimurium, Serratia marcesans* and *Pseudomonas* species. For example, *E. coli* K12 strain MM 294 (ATCC No. 31,446) is particularly useful. Other microbial strains that may be used include *E. coli* strains such as *E. coli* B and *E. coli* X1776 (ATCC No. 31,537). These examples are, of course, intended to be illustrative rather than limiting.

To express of peptides of the invention (or a functional derivative thereof) in a prokaryotic cell, it is necessary to operably link the peptide-encoding sequence to a functional prokaryotic promoter. Such promoters may be either constitutive or, more preferably, regulatable (i.e., inducible or derepressible). Examples of constitutive promoters include the int promoter of bacteriophage lambda., the bla promoter of the .beta.-lactamase gene sequence of pBR322, and the CAT promoter of the chloramphenicol acetyl transferase gene sequence of pPR325, and the like. Examples of inducible prokaryotic promoters include the major right and left promoters of bacteriophage lambda. (P.sub.L and P.sub.R), the trp, recA, .lambda.acZ, .lambda.acl, and gal promoters of *E. coli*, the .alpha.-amylase (Ulmanen et al., (1985) *J. Bacteriol.* 162:176–182) and the .zeta.-28-specific promoters of *B. subtilis* (Gilman et al., (1984) *Gene sequence* 32:11–20), the promoters of the bacteriophages of *Bacillus* (Gryczan, In: The Molecular Biology of the Bacilli, Academic Press, Inc., NY (1982)), and Streptomyces promoters (Ward et al., (1986) *Mol. Gen. Genet.* 203:468–478). The most commonly used in recombinant DNA construction promotors include the P-lactamase (penicillinase) and lactose promoter systems (Chang et al., (1978) *Nature*, 375: 615; Itakura et al., (1977) *Science*, 198, 1056; Goeddel et al., (1979) *Nature,* 281, 544) and a tryptophan (trp) promoter system (Goeddel et al., (1980) *Nucleic Acids Res.,* 8:4057; EPO Appl. Publ. No. 0036,776). While these are the most commonly used, other microbial promoters have been discovered and utilized, and details concerning their nucleotide sequences have been published, enabling a skilled worker to ligate them functionally with plasmid vectors (see, e., Siebenlist et al., (1980) *Cell,* 20, 269.

Proper expression in a prokaryotic cell also requires the presence of a ribosome binding site upstream of the gene sequence-encoding sequence. Such ribosome binding sites are disclosed, for example, by Gold et al. ((1981) *Ann. Rev. Microbiol.* 35:365–404). The ribosome binding site and other sequences required for translation initiation are operably linked to the nucleic acid molecule encoding peptides of invention. Translation in bacterial system is initiated at the codon with encode the first methionine. For this reason, it is preferable to include the ATG codon in peptide sequence and to ensure that the linkage between a promoter and a DNA sequence that encodes a peptide does not contain any intervening codons that are capable of encoding a methionine.

In addition to prokaryotes, eukaryotic organisms, such as yeast, or cells derived from multicellular organisms can be used as host cells. *Saccharomyces cerevisiae,* or common baker's yeast, is the most commonly used among eukaryotic microorganisms, although a number of other strains are commonly available. For expression in *Saccharomyces,* the plasmid YRp7, for example (Stinchcomb et al., (1979) *Nature* 282:39; Kingsman et al., (1979) *Gene* 7:141; Tschemper et al., (1980) *Gene* 10:157), is commonly used. This plasmid already contains the trp1 gene that provides a selection marker for a mutant strain of yeast lacking the ability to grow in tryptophan, for example, ATCC No. 44,076 or PEP4-1 (Jones, (1977) *Genetics,* 85, 12). The presence of the trp1 lesion as a characteristic of the yeast host cell genome then provides an effective environment for detecting transformation by growth in the absence of tryptophan. Suitable promoting sequences in yeast vectors include the promoters for 3-hosphoglycerate kinase (Hitzeman et al., (1980) *J. Biol. Chem.* 255:2073) or other glycolytic enzymes (Hess et al., (1968) *J. Adv. Enzyme Reg.* 7:149; Holland et al., (1978) *Biochemistry* 17:4900), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions, are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

In addition, plant cells are also available as hosts, and control sequences compatible with plant cells are available, such as the cauliflower mosaic virus 35S and 19S, and nopaline synthase promoter and polyadenylation signal sequences. Another preferred host is an insect cell, for example the Drosophila larvae. Using insect cells as hosts, the Drosophila alcohol dehydrogenase promoter can be used. Rubin, (1988) *Science* 240:1453–1459.

However, peptides of present invention can be expressed in vertebrata host cells. The propagation of vertebrate cells in culture (tissue culture) has become a routine procedure in recent years (Tissue Culture, Academic Press, Kruse and Patterson, editors (1973). Examples of useful mammalian host cells include monkey kidney CV1 line transformed by SV40 (COS-7, ATCC CRL 1651); human embryonic kidney line (293 or 293 cells subcloned for growth in suspension culture, Graham et al., (1977) *J. Gen Virol.,* 36: 59); baby hamster kidney cells (BHK, ATCC CCL 10); Chinese hamster ovary cells/-DHFR (CHO, Urlaub and Chasin, (1980) *Proc. Natl. Acad. Sci. USA,* 77:4216); mouse sertoli cells (TM4, Mather, (1980) *Biol. Reprod.,* 23: 243–251); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., (1982) *Annals N.Y. Acad. Sci.,* 383: 44–68); MRC 5 cells; FS4 cells; and a human hepatoma cell line (Hep G2). For expression in mammalian host cells, useful vectors include, but not limited vectors derived from SV40, vectors derived from cytomegalovirus such as the pRK vectors, including pRK5 and pRK7 (Suva et al., (1987) *Science,* 237:893–896, EP 307,247 (Mar. 15, 1989), EP 278,776 (Aug. 17, 1988)) vectors derived from vaccinia viruses or other pox viruses, and retroviral vectors such as vectors derived from Moloney's murine leukemia virus (MoMLV).

The expression of peptides of invention in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., (1982) *J. Mol. Appl. Gen.* 1:273–288); the TK promoter of Herpes virus (McKnight, (1982) *Cell* 31:355–365); the SV40 early promoter (Benoist et al., (1981) *Nature* (London) 290:304–310); the yeast gal4 gene sequence promoter (Johnston et al., (1982) *Proc. Natl. Acad. Sci. (USA)* 79:6971–6975; Silver et al., (1984) *Proc. Natl. Acad. Sci. (USA)* 81:5951–5955). An origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient. Satisfactory amounts of protein are produced by cell cultures; however, refinements, using a secondary coding sequence, serve to enhance production levels even further. One secondary coding sequence comprises dihydrofolate reductase (DHFR that is affected by an externally controlled parameter, such as methotrexate (MTX), thus permitting control of expression by control of the methotrexate concentration (Urlaub and Chasin, (1980) *Proc. Natl. Acad, Sci.* (USA) 77, 4216).

Optionally, the DNA encoding peptides of invention is operably linked to a secretory leader sequence resulting in secretion of the expression product by the host cell into the culture medium. Examples of secretory leader sequences include stII, ecotin, lamB, herpes GD, lpp, alkaline phsophatase, invertase, and alpha factor. Also suitable for use herein is the 36 amino acid leader sequence of protein A (Abrahmsen et al., (1985) *EMBO J.,* 4: 3901).

Once the vector or nucleic acid molecule containing the construct(s) has been prepared for expression, the DNA construct(s) may be introduced into an appropriate host cell by any of a variety of suitable means, i.e., transformation, transfection, conjugation, protoplast fusion, electroporation, particle gun technology, lipofection, calcium phosphate precipitation, direct microinjection, DEAE-dextran transfection, and the like. The most effective method for transfection of eukaryotic cell lines with plasmid DNA varies with the given cell type. After the introduction of the vector, recipient cells are grown in a selective medium, which selects for the growth of vector-containing cells. Expression of the cloned gene molecule(s) results in the production of peptides of invention. This can take place in the transformed cells as such, or following the induction of these cells to differentiate (for example, by administration of bromodeoxyuracil to neuroblastoma cells or the like). A variety of incubation conditions can be used to form the peptide of the present invention. The most preferred conditions are those which mimic physiological conditions.

Transfection refers to the taking up of an expression vector by a host cell whether or not any coding sequences are in fact expressed. Numerous methods of transfection are known to the ordinarily skilled artisan, for example, $CaPO_4$.precipitation and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., Molecular Cloning (2nd ed.), Cold Spring Harbor Laboratory, New York (1989), is generally used for prokaryotes or other cells that contain substantial cell-wall barriers. Infection with *Agrobacterium tumefaciens* is used for transformation of certain plant cells, as described by Shaw et al., (1983) *Gene*, 23: 315 and WO 89/05859 published 29 Jun. 1989. For mammalian cells without such cell walls, the calcium phosphate precipitation method described in section 16.30–16.37 of Sambrook et al., supra, is preferred. General aspects of mammalian cell host system transformations have been described by Axel in U.S. Pat. No. 4,399,216 issued Aug. 16, 1983. Transformations into yeast are typically carried out according to the method of Van Solingen et al., *J. Bact.*, 130: 946 (1977) and Hsiao et al., *Proc. Natl. Acad. Sci.* (*USA*), 76: 3829 (1979). However, other methods for introducing DNA into cells such as by nuclear injection, electroploration, or by protoplast fusion may also be used.

The host cells used to produce the peptides of invention can be cultured in a variety of media. as described generally in Sambrook et al. A wide variety of transcriptional and translational regulatory sequences may be employed, depending upon the nature of the host to control the expression. Transcriptional initiation regulatory signals may be selected which allow for repression or activation, so that expression of the gene sequences can be modulated. Of interest are regulatory signals, which are temperature-sensitive so that by varying the temperature, expression can be repressed or initiated, or are subject to chemical (such as metabolite) regulation.

In an intracellular expression system or periplasmic space secretion system, the recombinantly expressed peptides of invention can be recovered from the culture cells by disprupting the host cell membrane/cell wall (eg by osmotic shock or solubilizing the host cell membrane in detergent). Alternatively, in an extracellular secretion system, the recombinant peptide can be recovered from the culture medium. As a first step, the culture medium or lysate is centrifuged to remove any particulate cell debris. The membrane and soluble protein fractions are then separated. The Z domain variant peptide can then be purified from the soluble protein fraction. If the peptide is expressed as a membrane bound species, the membrane bound peptide can be recovered from the membrane fraction by solubilization with detergents. The crude peptide extract can then be further purified by suitable procedures such as fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; hydrophobic affinity resins and ligand affinity using IgG ligand immobilized on a matrix. In vitro transcription/translation systems can also be employed to produce peptides of the present invention using RNAs derived from the SEQ ID NO: 1 encoding DNA constructs. Cell-free translation systems have been used in the biosynthesis of proteins and peptides, and have become a standard tool in molecular biology for protein production (In vitro transcription and translation protocols, Methods in Molecular Biology, 37 Edited by M. J. Tymms, 1995, Humana Press. Inc., Merrick, Translation of exogenous mRNAs in reticulocyte lysates, *Meth. Enzymol.* 101:38 (1983)). Kigawa, T. and Yokohama, S., "Continuous Cell-Free Protein Synthesis System for Coupled Transcription-Translation" Journal of Biochemistry 110:166–168 (1991), Baranov et al., "Gene expression in a cell-free system on the preparative scale" (1989) *Gene* 84:463–466, Kawarasaki et al., "A long-lived batch reaction system of cell-free protein synthesis" (1995) *Analytical Biochemistry* 226:320–324). Both eukaryotic and prokaryotic cell-free systems can be used for in vitro SEQ ID NO: 1 synthesis. The rabbit reticulocyte (Pelham and Jackson, (1976) *Eur. J. Biochem.*, 67: 247–256) and wheat germ lysate (Roberts and Paterson, (1973) *Proc. Natl. Acad. Sci.*, 70: 2330–2334) methods are commonly used eukaryotic in vitro translation systems. The *E. coli* S30 extract method devised by Spirin, A. S. et al., "Continuous Cell-Free Translation System Capable of Producing Polypeptides in High Yield" (1988) *Science* 242 (4882): 1162–1164, Zubay, (1973) *Ann. Rev. Genet.*, 7:267, and the fractionated method of Gold and Schweiger, (1971) *Meth. Enzymol.*, 20: 537 are widely used prokaryotic in vitro translation systems.

The expression unit for in vitro synthesis comprises a 5' untranslated region and may additionally comprise a 3' region. The 5' untranslated region of the expression unit contains a promoter or RNA polymerase binding sequence, a ribosome binding sequence, and a translation initiation signal. The 5' untranslated region ("head") may also contain convenient restriction sites and a translation enhancer or "Activator" sequence(s). The 3' region may contain convenient restriction sites and a 3' tail of a selected sequence. The expression unit may be chemically synthesized by protocols well known to those skilled in the art. Alternatively, these elements may be incorporated into one or more plasmids, amplified in microorganisms, purified by standard procedures, and cut into appropriate fragments with restriction enzymes before assembly into the expression unit.

The 5' untranslated region contains a promoter or RNA polymerase binding sequence, such as those for the T7, T3, or SP6 RNA polymerase. Positioned downstream of or within the promoter region is a DNA sequence, which codes for a ribosomal binding site. This ribosome binding site may be specific for prokaryotic ribosomal complexes (including ribosomal RNAs) if a prokaryotic translation procedure is used. However, a preferred embodiment of this invention uses a eukaryotic sequence and an in vitro eukaryotic translation system, such as the rabbit reticulocyte system (Krawetz et al., 1983 *Can. J. Biochem. Cell. Biol.* 61:274–286; Merrick, 1983 *Meth. Enzymol.* 101:38). A consensus translation initiation sequence, GCCGCCAC-CATGG (SEQ ID NO: 33), well as other functionally related sequences have been established for vertebrate mRNAs (Kozak, 1987 *Nucleic Acids Res,* 15:8125–8148). This sequence or related sequences may be used in the DNA construction to direct protein synthesis in vitro. The ATG triplet in this initiation sequence is the translation initiation codon for methionine; in vitro protein synthesis is expected to begin at this point.

Between the promoter and translation initiation site, it may be desirable to place other known sequences, such as translation enhancer or "activator" sequences. For example, Jobling et al. (1988 *Nucleic Acids Res.* 16:4483–4498) showed that the untranslated "leader sequences" from tobacco mosaic virus "stimulated translation significantly" in SP6-generated mRNAs. They also reported that the 36-nucleotide 5' untranslated region of alfalfa mosaic virus RNA 4 increases the translational efficiency of barley amylase and human interleukin mRNAs (Jobling and Gehrke, 1987 *Nature* 325:622–625). Black beetle virus (Nodavirus) RNA 2 (Friesen and Rueckert, J. 1981 *Virol.* 37:876–886), turnip mosaic virus, and brome mosaic virus coat protein mRNAs (Zagorski et al., *Biochimie* 65:127–133, 1983) also translate at high efficiencies. In contrast, certain untranslated leaders severely reduce the expression of the SP6 RNAs (Jobling et al. (1988 *Nucleic Acids Res.* 16:4483–4498).

In addition, SEQ ID NO: 1 encoding DNA may be incorporated into the in vitro expression unit. Within one embodiment, the expressed polypeptides contain both carrier polypeptide/peptide and SEG ID NO 1. The carrier peptide would be useful for quantifying the amount of fusion polypeptide and for purification (given that an antibody against the carrier polypeptide is available or can be produced). One example is 6His amino acid sequence (SEQ ID NO: 40); the second is the 11 amino acid Substance P, which can be attached as fusion peptides to peptides of the invention. Anti-6 His (6×His: SEQ ID NO: 40) and anti-Substance P antibodies are commercially available for detecting and quantifying fusion proteins. Another example is the eight amino acid marker peptide, "Flag" (Hopp et al., 1988 *Bio/Technology* 6:1204–1210). A preferable form of the carrier polypeptide is one, which may be cleaved from the novel polypeptide by simple chemical or enzymatic means.

IV. Derivatives of Peptide

As used herein, the term "amino acid" and any reference to a specific amino acid is meant to include naturally occurring proteogenic amino acids as well as non-naturally occurring amino acids such as amino acid analogs. One of skill in the art would know that this definition includes, unless otherwise specifically indicated, naturally occurring proteogenic (D) or (L) amino acids, chemically modified amino acids, including amino acid analogs such as penicillamine (3-mercapto-D-valine), naturally occurring non-proteogenic amino acids such as norleucine and chemically synthesized compounds that have properties known in the art to be characteristic of an amino acid. As used herein, the term "proteogenic" indicates that the amino acid can be incorporated into a protein in a cell through well-known metabolic pathways.

The choice of including an (L)- or a (D)-amino acid into a peptide of the present invention depends, in part, on the desired characteristics of the peptide. For example, the incorporation of one or more (D)-amino acids can confer increasing stability on the peptide in vitro or in vivo. The incorporation of one or more (D)-amino acids also can increase or decrease the binding activity of the peptide as determined, for example, using the binding assays described herein, or other methods well known in the art. In some cases it is desirable to design a peptide that retains activity for a short period of time, for example, when designing a peptide to administer to a subject. In these cases, the incorporation of one or more (L)-amino acids in the peptide can allow endogenous peptidases in the subject to digest the peptide in vivo, thereby limiting the subject's exposure to an active peptide.

As used herein, the term "amino acid equivalent" refers to compounds, which depart from the structure of the naturally occurring amino acids, but which have substantially the structure of an amino acid, such that they can be substituted within a peptide, which retains is biological activity. Thus, for example, amino acid equivalents can include amino acids having side chain modifications or substitutions, and also include related organic acids, amides or the like. The term "amino acid" is intended to include amino acid equivalents. The term "residues" refers both to amino acids and amino acid equivalents.

As used herein, the term "peptide" is used in its broadest sense to refer to compounds containing amino acid equivalents or other non-amino groups, while still retaining the desired functional activity of a peptide. Peptide equivalents can differ from conventional peptides by the replacement of one or more amino acids with related organic acids (such as PABA), amino acids or the like or the substitution or modification of side chains or functional groups.

It is to be understood that limited modifications can be made to a peptide without destroying its biological function. Thus, modification of the peptides of the present invention that do not completely destroy their activity is within the definition of the compound claims as such. Modifications can include, for example, additions, deletions, or substitutions of amino acids residues, substitutions with compounds that mimic amino acid structure or functions, as well as the addition of chemical moieties such as amino or acetyl groups. The modifications can be deliberate or accidental, and can be modifications of the composition or the structure.

As used herein, "binding" refers to the ability of a given peptide to interact with a receptor such that the interaction between the peptide and the receptor is relatively specific. As used herein, the term "relatively specific" means that the affinity of binding of the receptor and peptide is about $1\times10^{-5}$M or less. Therefore, the term "binding" does not encompass non-specific binding, such as non-specific adsorption to a surface. Non-specific binding can be readily identified by including the appropriate controls in a binding assay. Methods for determining the binding affinity are described in the Examples below.

The peptides of the present invention are as well useful when they are maintained in a constrained secondary conformation. As used herein, the terms "constrained secondary structure," "stabilized" and "conformationally stabilized" indicate that the peptide bonds comprising the peptide are not able to rotate freely but instead are maintained in a relatively fixed structure.

Various methods for constraining the secondary structure of a peptide are well known in the art. For example, peptides such as those containing -Phe-Pro-Gly-Phe-sequence (SEQ ID NO: 37) form -turn, a well-known secondary structure. For example, a peptide can be stabilized by incorporating it into a sequence that forms a helix such as an alpha helix or a triple helix, according to methods described, for example, by Dedhar et al., (1987) *J. Cell. Biol.* 104:585; by Rhodes et al., (1978) *Biochem* 17:3442; and by Carbone et al., (1987) *J. Immunol* 138:1838, each of which is incorporated herein by reference. Additionally, the peptides can be incorporated into larger linear, cyclic or branched peptides, so long as their receptor-binding activity is retained. The peptides of the present invention may be of any size so long as the VEGF receptor-binding activity is retained, however, in one embodiment, peptides having twenty or fewer total amino acids are preferred.

A preferred method for constraining the secondary structure of a newly synthesized linear peptide is to cyclize the peptide using any of various methods well known in the art. For example, a cyclized peptide of the present invention can be prepared by forming a peptide bond between non-adjacent amino acid residues as described, for example, by Schiller et al., (1985) *Int. J. Pept. Prot. Res.* 25:171, which is incorporated herein by reference. Peptides can be synthesized on the Merrifield resin by assembling the linear peptide chain using $N^\alpha$-Fmoc-amino acids with Boc and tertiary-butyl side chain protection. Following the release of the peptide from the resin, a peptide bond can be formed between the amino and carboxy termini.

A newly synthesized linear peptide can also be cyclized by the formation of a bond between reactive amino acid side chains. For example, a peptide containing a cysteine-pair can be synthesized and a disulfide bridge can be formed by oxidizing a dilute aqueous solution of the peptide with $K_3[Fe(CN)_6]$. Alternatively, a lactam such as an ←($\varsigma$-glutamyl)-lysine bond can be formed between lysine and glutamic acid residues, a lysinonorleucine bond can be formed between lysine and leucine residues or a dityrosine bond can be formed between two tyrosine residues. Cyclic peptides can be constructed to contain, for example, four lysine residues, which can form the heterocyclic structure of desmosine (see, for example, Devlin, Textbook of Biochemistry 3rd ed. (1992), which is herein incorporated by reference).

Methods for forming these and other bonds are well known in the art and are based on well-known rules of chemical reactivity (Morrison and Boyd, Organic Chemistry, 6th Ed. (Prentice Hall, 1992), which is herein incorporated by reference).

V. Peptidoimetics

Peptide analogs are commonly used in the pharmaceutical industry as non-peptide drugs with properties analogous to those of the template peptide. These types of non-peptide compound are termed "peptide mimetics" or "peptidomimetics" (Fauchere, J. (1986) *Adv. Drug Res.* 15: 29; Veber and Freidinger (1985) *TINS* p. 392; and Evans et al. (1987) *J. Med. Chem* 30: 1229, which are incorporated herein by reference) and can be developed, for example, with the aid of computerized molecular modeling.

In a preferred embodiment, the present invention provides a pharmaceutical composition comprising at least one polypeptide or derivative thereof, wherein the polypeptide or derivative thereof is capable of specific binding with the high affinity VEGF receptor-1 or a derivative of the VEGF receptor-1 and structural similar receptors comprises the amino acid sequence of SEQ ID NO: 1 wherein the derivatives of SEQ ID NO: 1 comprises peptidomimetics that are capable of specific binding with the high affinity VEGF receptor-1 or a derivative of the VEGF receptor-1.

Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as SEQ ID NO:1, but have one or more peptide linkages optionally replaced by a linkage selected from the group consisting of: —$CH_2$—NH—, —$CH_2$S—, —$CH_2$—$CH_2$—, —CH=CH— (cis and trans), —$COCH_2$—, —CH(OH)$CH_2$—, and —$CH_2$SO—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., Vega Data (March 1983), Vol. 1, Issue 3, "Peptide Backbone Modifications" (general review); Morley, J. S., Trends Pharm Sci (1980) pp. 463–468 (general review); Hudson, D. et al., (1979) *Int J Pept Prot Re* 14:177–185 (—$CH_2$ NH—, —$CH_2$—$CH_2$—); Spatola, A. F. et al., (1986) *Life Sci* 38:1243–1249 (—$CH_2$—S); Hann, M. M., (1982) *J Chem Soc Perkin Trans I* 307–314 (—CH=CH—, cis and trans); Almquist, R. G. et al., (1980) *J Med Chem* 23: 1392–1398 (—$COCH_2$—); Jennings-White, C. et al., (1982) *Tetrahedron Lett* 23:2533 (—$COCH_2$—); Szelke, M. et al., European Appln. EP 45665 (1982) CA: 97:39405 (1982) (—CH(OH)$CH_2$—); Holladay, M. W. et al., (1983) *Tetrahedron Lett* 24:4401–4404 (—C(OH)$CH_2$—); and Hruby, V. J., (1982) *Life Sci* 31:189–199 (—$CH_2$—S—); each of which is incorporated herein by reference.

In another embodiment, a particularly preferred non-peptide linkage is —$CH_2$NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others.

Labeling of peptidomimetics usually involves covalent attachment of one or more labels, directly or through a spacer (eg., an amide group), to non-interfering position(s) on the peptidomimetic that are predicted by quantitative structure-activity data and/or molecular modeling. Such non-interfering positions generally are positions that do not form direct contacts with the macromolecules(s) (e.g., are not contact points in VEGFR-VEGF complexes) to which the peptidomimetic binds to produce the therapeutic effect. Derivitization (e.g., labelling) of peptidomimetics should not substantially interfere with the desired biological or pharmacological activity of the peptidomimetic.

A variety of designs for peptide mimetics are possible. For example, cyclic peptides, in which the necessary conformation for binding is stabilized by nonpeptides, are specifically contemplated. U.S. Pat. No. 5,192,746 to Lobl, et al., U.S. Pat. No. 5,169,862 to Burke, Jr., et al, U.S. Pat. No. 5,539,085 to Bischoff, et al., U.S. Pat. No. 5,576,423 to Aversa, et al., U.S. Pat. No. 5,051,448 to Shashoua, and U.S. Pat. No. 5,559,103 to Gaeta, et al., all hereby incorporated by reference, describe multiple methods for creating such compounds. Synthesis of nonpeptide compounds that mimic peptide sequences is also known in the art. Eldred, et al., (*J. Med. Chem.* 37:3882 (1994)) describe nonpeptide antagonists that mimic the peptide sequence. Likewise, Ku, et al., (*J. Med. Chem.* 38:9 (1995)) give further elucidation of the synthesis of a series of such compounds.

Derivatives of SEQ ID NO:1 can be produced using recombinant nucleic acid molecule techniques. Modifications to a specific peptide may be deliberate, as through site-directed mutagenesis and amino acid substitution during biosynthesis, or may be accidental such as through mutations in hosts, which produce the peptide. Peptides including derivatives can be obtained using standard mutagenesis techniques such as those described in Sambrook et al., Molecular Cloning, Cold Spring Harbor Laboratory Press (1989). For example, Chapter 15 of Sambrook describes procedures for site-directed mutagenesis of cloned DNA.

Derivatives of SEQ ID NO: 1 include, but not limited by modification occurring during or after translation, for example, by phosphorylation, glycosylation, crosslinking, acylation, proteolytic cleavage, linkage to a therapeutic protein, an antibody molecule, membrane molecule or other ligand (see Ferguson et al., 1988, *Annu. Rev. Biochem.* 57:285–320).

Specific types of genetically produced derivatives also include, but not limit by amino acid alterations such as deletions, substitutions, additions, and amino acid modifications. A "deletion" refers to the absence of one or more amino acid residue(s) in the related peptide. An "addition" refers to the presence of one or more amino acid residue(s) in the related peptide. Additions and deletions to a peptide may be at the amino terminus, the carboxy terminus, and/or internal, can be produced by mutation in SEQ ID NO: 1 encoding DNA and/or by peptide post-translation modification.

Amino acid "modification" refers to the alteration of a naturally occurring amino acid to produce a non-naturally occurring amino acid. Analogs of SEQ ID NO: 1 with unnatural amino acids can be created by site-specific incorporation of unnatural amino acids into polypeptides during the biosynthesis, as described in Christopher J. Noren, Spencer J. Anthony-Cahill, Michael C. Griffith, Peter G. Schultz, 1989 *Science*, 244:182–188.

A "substitution" refers to the replacement of one or more amino acid residue(s) by another amino acid residue(s) in the peptide. Mutations can be made in SEQ ID NO: 1 encoding DNA such that a particular codon is changed to a codon, which codes for a different amino acid. Such a mutation is generally made by making the fewest nucleotide changes possible. A substitution mutation of this sort can be made to change an amino acid in the resulting peptide in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting peptide. To some extent the following groups contain amino acids which are interchangeable: the basic amino acids lysine, arginine, and histidine; the acidic amino acids aspartic and glutamic acids; the neutral polar amino acids serine, threonine, cysteine, glutamine, asparagine and, to a lesser extent, methionine; the nonpolar aliphatic amino acids glycine, alanine, valine, isoleucine, and leucine (however, because of size, glycine and alanine are more closely related and valine, isoleucine and leucine are more closely related); and the aromatic amino acids phenylalanine, tryptophan, and tyrosine. In addition, although classified in different categories, alanine, glycine, and serine seem to be interchangeable to some extent, and cysteine additionally fits into this group, or may be classified with the polar neutral amino acids. Although proline is a nonpolar neutral amino acid, its replacement represents difficulties because of its effects on conformation. Thus, substitutions by or for proline are not preferred, except when the same or similar conformational results can be obtained. The conformation conferring properties of proline residues may be obtained if one or more of these is substituted by hydroxyproline (Hyp). Derivatives can contain different combinations of alterations including more than one alteration and different types of alterations.

The ability of the derivative to retain some activity can be measured using techniques described herein and/or using techniques known to those skilled in the art for measuring the VEGF receptor-1 binding activity. "Derivatives" of SEQ ID NO: 1 are functional equivalents having similar amino acid sequence and retaining, to some extent, the activities of SEQ ID NO:1. By "functional equivalent" is meant the derivative has an activity that can be substituted for the activity of SEQ ID NO:1. Preferred functional equivalents retain the full level of VEGF receptor-1-binding activity as measured by assays known to these skilled in the art, and/or in the assays described herein. Preferred functional equivalents have activities that are within 1% to 10,000% of the activity of SEQ ID NO:1, more preferably between 10% to 1000%, and more preferably within 50% to 200%. Derivatives have at least 50% sequence similarity, preferably 70%, more preferably 90%, and even more preferably 95% sequence similarity to SEQ ID NO:1. "Sequence similarity" refers to "homology" observed between amino acid sequences in two different polypeptides, irrespective of polypeptide origin.

VI. Biological Agents

A variety of biological agents are suitable for use in the invention. These include, without limitation, proteins, peptides (e.g., oligopeptides and polypeptides) including cytokines, hormones (such as insulin), and the like, recombinant soluble receptors, monoclonal antibodies, human growth hormones, tissue plasminogen activators, clotting factors, vaccines, colony stimulating factors, erythropoietins, enzymes, and dismultase. Therefore, in on embodiment, the present pharmaceutical composition comprising at least one polypeptide or derivative thereof, wherein the polypeptide or derivative thereof is capable of specific binding with the high affinity VEGF receptor-1 or a derivative of the VEGF receptor-1 and structural similar receptors further comprises a biological agent.

Preferred classes of biological agents (including chemotherapeutic agents) include anti-neoplastic agents, antibacterial agents, antiparasitic agents, anti-fungal agents, CNS agents, immunomodulators and cytokines, toxins and neuropeptides. Biological agents for which target cells tend to develop resistance mechanisms are also preferred. Particularly preferred biological agents include anthracyclines such as doxorubicin, daunorubicin, epirubicin, idarubicin, mithoxanthrone or carminomycin, vinca alkaloids, mitomycin-type antibiotics, bleomycin-type antibiotics, azole antifungals such as fluconazole, polyene antifungals such as amphotericin B, taxane-related antineoplastic agents such as paclitaxel and immunomodulators such as tumor necrosis factor alpha (TNF-α), interferons and cytokines.

Preferred biological agents (including chemotherapeutic agents) include without limitation additional antifungal agents such as amphotericin-B, flucytosine, ketoconazole, miconazole, itraconazole, griseofulvin, clotrimazole, econazole, terconazole, butoconazole, ciclopirox olamine, haloprogin, toinaftate, naftifine, nystatin, natamycin, undecylenic acid, benzoic acid, salicylic acid, propionic acid and caprylic acid. Such agents further include without limitation antiviral agents such as zidovudine, acyclovir, ganciclovir, vidarabine, idoxuridine, trifluridine, foxcarnet, amantadine, rimantadine and ribavirin. Such agents further include without limitation antibacterial agents such as penicillin-related compounds including 9-lactam antibiotics, broad spectrum penicillins and penicillinase-resistant penicillins (such as methicillin, nafcillin, oxacillin, cloxacillin, dicloxacillin, amoxicillin, ampicillin, ampicillin-sulbactam, azocillin, bacampicillin, carbenicillin, carbenicillin indanyl, cyclacillin, mezlocillin, penicillin G, penicillin V, piperacillin, ticarcillin, imipenem and aztreonam), cephalosporins (cephalosporins include first generation cephalosporins such as cephapirin, cefaxolin, cephalexin, cephradine and cefadroxil; second generation cephalosporins such as cefamandole, cefoxitin, cefaclor, cefuroxime, cefuroxime axetil, cefonicid, cefotetan and ceforanide; third generation cephalosporins such as cefotaxime, ceftizoxime, ceftriaxone, cefoperazone and ceftazidime), tetracyclines (such as demeclocytetracycline, doxycycline, methacycline, minocycline and oxytetracycline), beta-lactamase inhibitors (such as clavulanic acid), aminoglycosides (such as amikacin, gentamicin C, kanamycin A, neomycin B, netilmicin, streptomycin and tobramycin), chloramphenicol, erythromycin, clindamycin, spectinomycin, vancomycin, bacitracin, isoniazid, rifampin, ethambutol, aminosalicylic acid, pyrazinamide, ethionamide, cycloserine, dapsone, sulfoxone sodium, clofazimine, sulfonamides (such as sulfanilamide, sulfamethoxazole, sulfacetamide, sulfadiazine, and sulfisoxazole), trimethoprim-sulfamethoxazole, quinolones (such as nalidixic acid, cinoxacin, norfloxacin and ciprofloxacin), methenamine, nitrofurantoin and phenazopyridine. Such agents further include agents active against protozoal infections such as chloroquine, diloxanide furoate, emetine or dehydroemetine, 8-hydroxyquinolines, metronidazole, quinacrine, melarsoprol, nifurtimox, pentamidine, sodium stibogluconate and suramin.

A variety of central nervous system agents are suitable for use in the present composition. These include neuroleptics such as the phenothiazines (such as compazine, thorazine, promazine, chlorpromazine, acepromazine, aminopromazine, perazine, prochlorperazine, trifluoperazine, and thioproperazine), rauwolfia alkaloids (such as reserpine and deserpine), thioxanthenes (such as chlorprothixene and tiotixene), butyrophenones (such as haloperidol, moperone, trifluoperidol, timiperone, and droperidol), diphenylbutylpiperidines (such as pimozide), and benzamides (such as sulpiride and tiapride); tranquilizers such as glycerol derivatives(such as mephenesin and methocarbamol), propanediols (such as meprobamate), diphenylmethane derivatives (such as orphenadrine, benzotrapine, and hydroxyzine), and benzodiazepines(such as chlordiazepoxide and diazpam); hypnotics (such as zolpdem and butoctamide); 9-blockers (such as propranolol, acebutonol, metoprolol, and pindolol); antidepressants such as dibenzazepines (such as imipramine), dibenzocycloheptenes (such as amitriptyline), and the tetracyclics (such as mianserine); MAO inhibitors (such as phenelzine, iproniazide, and selegeline); psychostimulants such as phenylethylamine derivatives (such as amphetamines, dexamphetamines, fenproporex, phentermine, amfepramone, and pemline) and dimethylaminoethanols (such as clofenciclan, cyprodenate, amninorex, and mazindol); GABA-mimetics (such as progabide), alkaloids (such as co-dergocrine, dihydroergocristine, and vincamine); cholinergics (such as citicoiine and physosigmine); vasodilators (such as pentoxifyline); and cerebro active agents (such as pyritinol and meclofenoxate); as well as mixtures of several such agents.

Of particular interest are sedative-hypnotics such as the benzodiazepines, psycho-pharmacological agents such as the phenothiazines, thioxanthenes, butyrophenones, and dibenzoxazepines, and central nervous system stimulants. In one embodiment, the pharmaceutical composition of the present invention further comprises a biological agent that can be applied to a wide variety of central nervous system agents by applying the principles and procedures described herein.

The compositions also can utilize a variety of polypeptides such as antibodies, toxins such as diphtheria toxin, peptide hormones, such as colony stimulating factor, and tumor necrosis factors, neuropeptides, growth hormone, erythropoietin, and thyroid hormone, lipoproteins such as α-lipoprotein, proteoglycans such as hyaluronic acid, glycoproteins such as gonadotropin hormone, immunomodulators or cytokines such as the interferons or interleukins, hormone receptors such as the estrogen receptor. Preferred peptides are those with molecular weight of at least about 1,000, more preferably at least about 5,000, most preferably at least about 10,000. The compositions also can be utilize enzyme inhibiting agents such as reverse transcriptase inhibitors, protease inhibitors, angiotensin converting enzymes, 5α-reductase, and the like. Typical of these agents are peptide and nonpeptide structures such as finasteride, quinapril, ramipril, lisinopril, saquinavir, ritonavir, indinavir, nelfinavir, zidovudine, zalcitabine, allophenylnorstatine, kynostatin, delaviridine, bis-tetrahydrofuran ligands (see, for example Ghosh et al., *J. Med. Chem.* 39 (17): 3278–90 1966), and didanosine. Such agents can be administered alone or in combination therapy; e.g., a combination therapy utilizing saquinavir, zalcitabine, and didanosine or saquinavir, zalcitabine, and zidovudine. See, for example, Collier et al., *Antiviral Res.,* 1996 Jam. 29 (1): 99.

A variety of human and animal cytokines are suitable for use in the present compositions. These include interferons, interleukins, tumor necrosis factors (TNFs) such as TNFα, and a number of other protein and peptide factors controlling functions of the immune system. It will be appreciated that this extends to mixtures of several such agents, and the invention is not directed to the underlying specific activity of the cytokines themselves, but rather to the compositions themselves.

VII. Carriers

A variety of carriers can be associated with the ligand including, but not limiting by synthetic, semi-synthetic and natural compounds such as polypeptides, lipids, carbohydrates, polyamines, synthetic polymers, that form solutions (unimolecular systems), dispersions (supramolecular systems), or any particular systems such as nanoparticles, microspheres, matrixes, gels and other.

Therefore, in one embodiment, this invention provides a pharmaceutical composition comprising at least one polypeptide or derivative thereof, wherein said polypeptide or derivative thereof is capable of specific binding with the high affinity VEGF receptor-1 or a derivative of the VEGF receptor-1 and structural similar receptors further comprises a carrier. The invention further provides a pharmaceutical composition comprising one or more Ligands or their complex with a carrier in association with a biological agent The following classes of carriers are given as examples. It is understood, however, that a variety of other carriers can be used in the present invention.

The polymeric carriers can be nonionic water-soluble, nonionic hydrophobic or poorly water soluble, cationic, anionic or polyampholite, such as a polypeptides. It is preferred that the degrees of polymerization of these polymer carriers were from about 3 to about 500,000 more preferably from about 5 to about 5000, still more preferably from about 20 to about 500.

Preferred hydrophilic carrier is a nontoxic and non-immunogenic polymer which is soluble in water. Such segments include (but not are limited to) polyethers (e.g., polyethylene oxide), polysaccharides (e.g., dextran), polyglycerol, homopolymers and copolymers of vinyl monomers (e.g., polyacrylamide, polyacrylic esters (e.g., polyacryloyl morpholine), polymethacrylamide, poly(N-(2-hydroxypropyl)methacrylamide, polyvinyl alcohol, polyvinyl pyrrolidone, polyvinyltriazole, N-oxide of polyvinylpyridine, copolymer of vinylpyridine and vinylpyridine N-oxide) polyortho esters, polyaminoacids, polyglycerols (e.g., poly-2-methyl-2-oxazoline, poly-2-ethyl-2-oxazoline) and copolymers and derivatives thereof.

Preferred nonionic hydrophobic and poorly water soluble segments include polypropylene oxide, copolymers of polyethylene oxide and polyethylene oxide, polyalkylene oxide other than polyethylene oxide and polypropylene oxide, homopolymers and copolymers of styrene (e.g., polystyrene), homopolymers and copolymers isoprene (e.g., polyisoprene), homopolymers and copolymers butadiene (e.g., polybutadiene), homopolymers and copolymers propylene (e.g., polypropylene), homopolymers and copolymers ethylene (e.g., polyethylene), homopolymers and copolymers of hydrophobic amino acids and derivatives of amino acids (e.g., alanine, valine, isoleucine, leucine, norleucine, phenylalanine, tyrosine, tryptophan, threonine, proline, cistein, methionone, serine, glutamine, aparagine), homopolymers and copolymers of nucleic acid and derivatives thereof.

Preferred polyanionic carrier include those such as polymethacrylic acid and its salts, polyacrylic acid and its salts, copolymers of methacrylic acid and its salts, copolymers of acrylic acid and its salts, heparin, polyphosphate, homopolymers and copolymers of anionic amino acids (e.g., glutamic acid, aspartic acid), polymalic acid, polylactic acid, polynucleotides, carboxylated dextran, and the like.

Preferred polycationic carrier include polylysine, polyasparagine, homopolymers and copolymers of cationic amino acids (e.g., lysine, arginine, histidine), alkanolamine esters of polymethacrylic acid (e.g., poly-(dimethylammonioethyl methacrylate), polyamines (e.g., spermine, polyspermine, polyethyleneimine, polypropyleneimine, polybutileneimine, poolypentyleneimine, polyhexyleneimine and copolymers thereof), copolymers of tertiary amines and secondary amines, partially or completely quaternized amines, polyvinyl pyridine and the quaternary ammonium salts of the polycation segments. These preferred polycation segments also include aliphatic, heterocyclic or aromatic ionenes (Rembaum et al., *Polymer letters,* 1968, 6; 159; Tsutsui, T., In Development in ionic polymers-2, Wilson A. D. and Prosser, H. J. (eds.) Applied Science Publishers, London, N.Y. , vol. 2, pp. 167–187, 1986).

Additionally, dendrimers, for example, polyamidoamines of various generations (Tomalia et al., *Angew. Chem., Int. Ed. Engl.* 1990, 29, 138) can be also used.

Particularly preferred are copolymers selected from the following polymer groups:

(a) segmented copolymers having at least one hydrophilic nonionic polymer and at least one hydrophobic nonionic segment ("hydrophilic-hydrophobic copolymers");
(b) segmented copolymers having at least one cationic segment and at least one nonionic segment ("cationic copolymers");
(c) segmented copolymers having at least one anionic segment and at least one nonionic segment ("anionic copolymers");
(d) segmented copolymers having at least one polypetide segment and at least one non-peptide segment ("polypeptide copolymers");
(e) segmented copolymers having at least one polynucleotide segment and at least one segment which is not a nucleic acid "polypeptide copolymers");

Typical representatives of hydrophilic-hydrophobic copolymers are the block copolymers of ethylene oxide and propylene oxide having the formulas:

A. Copolymers of Ethylene Oxide and Propylene Oxide.

In one preferred embodiment, the segmented copolymers are the block copolymers of ethylene oxide and propylene oxide having the formulas:

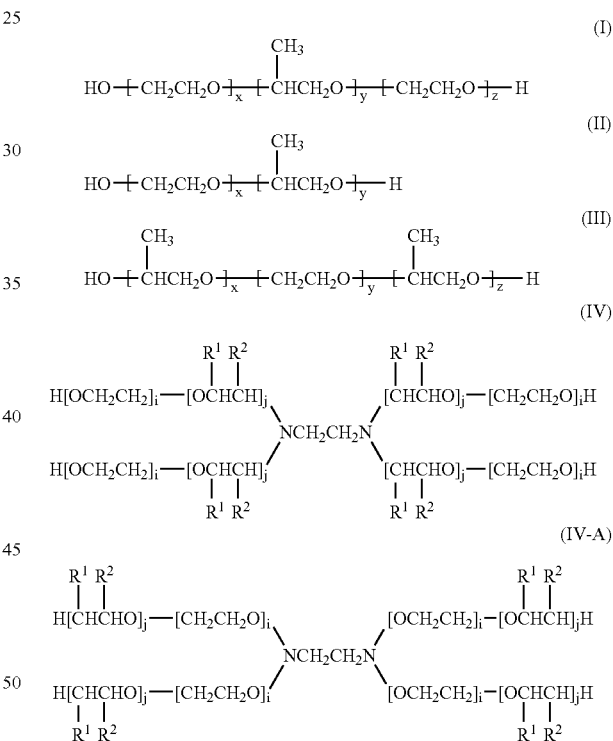

in which x, y, z, i and j have values from about 2 to about 800, preferably from about 5 to about 200, more preferably from about 5 to about 80, and wherein for each $R^1$, $R^2$ pair, one is hydrogen and the other is a methyl group.

Formulas (I) through (III) are oversimplified in that, in practice, the orientation of the isopropylene radicals within the B block will be random. This random orientation is indicated in formula (IV), which is more complete. Such poly(oxyethylene)-poly(oxypropylene) compounds have been described by Santon, *Am. Perfumer Cosmet.,* 72(4): 54–58 (1958); Schmolka, Loc. cit. 82(7):25 (1967); Schick, Non-ionic Surfactants, pp. 300–371 (Dekker, N.Y., 1967). A number of such compounds are commercially available under such generic trade names as "poloxamers", "pluronics" and "synperonics." Pluronic polymers within the B-A-B formula are often referred to as "reversed" pluronics, "Pluronic-R" or "meroxapol." The "polyoxamine" polymer of formula (XVII) is available from BASF (Wyandotte, Mich.) under the tradename TETRONIC™. The order of the polyoxyethylene and polyoxypropylene blocks represented in formula (XVII) can be reversed, creating TETRONIC-R™, also available from BASF. See, Schmolka, *J. Am. Oil Soc.,* 59:110 (1979). Polyoxypropylene-polyoxyethylene block copolymers can also be designed with hydrophilic blocks comprising a random mix of ethylene oxide and propylene oxide repeating units. To maintain the hydrophilic character of the block, ethylene oxide will predominate. Similarly, the hydrophobic block can be a mixture of ethylene oxide and propylene oxide repeating units. Such block copolymers are available from BASF under the tradename PLURADOT™.

The diamine-linked pluronic of formula (IV) can also be a member of the family of diamine-linked polyoxyethylene-polyoxypropylene polymers of formula:

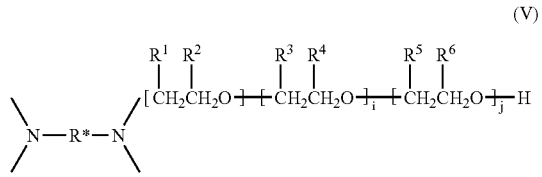

(V)

wherein the dashed lines represent symmetrical copies of the polyether extending off the second nitrogen, R* is an alkylene of 2 to 6 carbons, a cycloalkylene of 5 to 8 carbons or phenylene, for $R^1$ and $R^2$, either (a) both are hydrogen or (b) one is hydrogen and the other is methyl, for $R^3$ and $R^4$ either (a) both are hydrogen or (b) one is hydrogen and the other is methyl, if both of $R^3$ and $R^4$ are hydrogen, then one $R^5$ and $R^6$ is hydrogen and the other is methyl, and if one of $R^3$ and $R^4$ is methyl, then both of $R^5$ and $R^6$ are hydrogen.

Those of ordinary skill in the art will recognize, in light of the discussion herein, that even when the practice of the invention is confined for example, to poly(oxyethylene)-poly(oxypropylene) compounds, the above exemplary formulas are too confining. Thus, the units making up the first block need not consist solely of ethylene oxide. Similarly, not all of the B-type block need consist solely of propylene oxide units. Instead, the blocks can incorporate monomers other than those defined in formulas (I)–(V), so long as the parameters of the first embodiment are maintained. Thus, in the simplest of examples, at least one of the monomers in block A might be substituted with a side chain group as previously described.

A variety of other examples of hydrophilic-hyrophobic block copolymers have been synthesized that can be used in the present invention. These copolymers have the general formula $A_nB_m$, wherein A is the hydrophilic homopolymer or copolymer segment, and B is a hydrophobic homopolymer or copolymer segment. Each of the A and B segments can be either straight chain or branched. Examples of block copolymers that are particularly useful in the current invention include, but are not limited to poly(ethylene oxide)β-poly(isoprene)-β-poly(ethylene oxide) triblock copolymer (Morgan, et al., *Biochem. Soc. Trans.,* 18:1021, 1990), poly(ethylene oxide)-β-poly(styrene) block copolymer (Dunn, et al., *Pharm. Res.,* 11:1016, 1994), poly(ethylene oxide)-β-poly(D,L-lactide) diblock copolymer (Hagan, et al. Langmuir 12:2153, 1996), and poly(ethylene oxide)-β-poly ((-benzyl L-aspartate) diblock copolymer (Kwon, et al. Langmuir 12:945, 1993).

The hydrophilic homopolymer or copolymer A segments in hydrophilic-hyrophobic block copolymers that can be used in the present invention will contain at least three monomeric units, each of which unit will have the same or different pendant group. Each pendant group will contain at least one atom selected from the group consisting of oxygen and nitrogen. Representative hydrophilic homopolymers or copolymers include but are not limited to polyethylene oxides, copolymers of ethylene oxide and propylene oxide, polysaccharides, polyacrylamides, polygycerols, polyvinylalcohols, polyvinylpyrrolidones, polyvinylpyridine N-oxides, copolymers of vinylpyridine N-oxide and vinylpyridine, polyoxazolines, and polyacroylmorpholines.

Preferably, the hydrophilic A segment is:

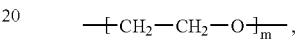

a copolymer of

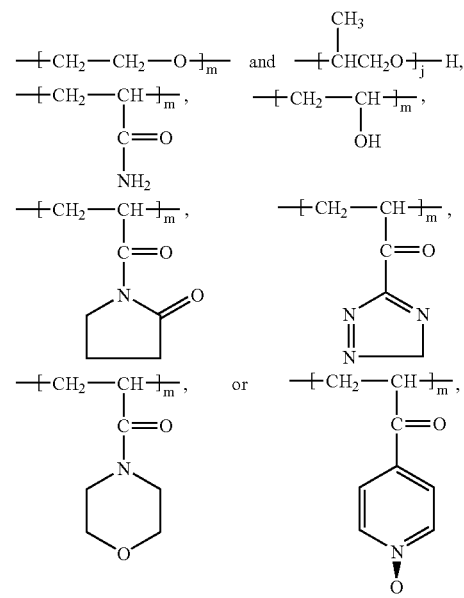

in which each of m and j has a value of from 3 to 5000.

The hydrophobic B segments useful in this invention can also contain fluorocarbon moieties including but not limited to fluoroalkyl segments, and copolymers containing both fluorocarbon and hydrocarbon. One such example is the segmented block copolymers having the formula:

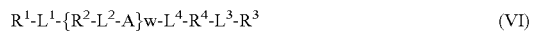

(VI)

in which:
either, (i) $R^1$ is a monovalent fluorinated hydrocarbon of 2 to 50 carbon atoms and $R^2$ is a divalent hydrocarbon of 2 to 50 carbon atoms or (ii) $R^1$ is a monovalent hydrocarbon of 2 to 50 carbon atoms and $R^2$ is a divalent fluorinated hydrocarbon of 2 to 50 carbon atoms;
$R^3$ is (i) hydrogen, (ii) a monovalent fluorinated hydrocarbon of 2 to 50 carbon atoms, or (iii) a monovalent hydrocarbon of 2 to 50 carbon atoms;

R[4] is (i) a bond if R[3] is hydrogen; (ii) a divalent hydrocarbon of 2 to 50 carbon atoms if R[3] is a fluorinated hydrocarbon, or (iii) a divalent fluorinated hydrocarbon of 2 to 50 carbon atoms if R[3] is a hydrocarbon;

each of $L^1$ and $L^2$, independently of the other, is a linking group;

$L^3$ and $L^4$ taken together with $R^4$, is a bond if $R^3$ is hydrogen or if $R^3$ is other than hydrogen each of $L^3$ and $L^4$, taken independently is a linking group;

A is a hydrophilic homopolymer or copolymer comprising at least three monomeric units each having the same or different pendant group containing at least atom selected from the group consisting of oxygen and nitrogen; and w has a value of from 1 to 100.

The hydrophilic homopolymer or copolymer A will contain at least three monomeric units, each of which unit will have the same or different pendant group. Each pendant group will contain at least one atom selected from the group consisting of oxygen and nitrogen. Representative hydrophilic homopolymers or copolymers include polyethylene oxides, copolymers of ethylene oxide and propylene oxide, polysaccharides, polyacrylamides, polyglycerols, polyvinylalcohols, polyvinylpyrrolidones, polyvinylpyridine N-oxides, copolymers of vinylpyridine N-oxide and vinylpyridine, polyoxazolines, and polyacroylmorpholines.

B. Cationic Copolymers.

Useful segmented copolymers include a class of copolymers in which at least one segment is a polycation. One example of these structures is a basis of copolymers comprising a plurality of covalently bound polymer segments wherein the segments have (a) at least one polycation segment which segment is a cationic homopolymer, copolymer, or block copolymer comprising at least three aminoalkylene monomers, the monomers being selected from the group consisting of at least one of the following:

(i) at least one tertiary amino monomer of the formula:

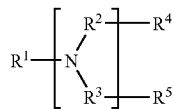
A.

and the quaternary salts of the tertiary amino monomer, or
(ii) at least one secondary amino monomer of the formula:

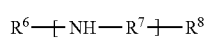
B.

and the acid addition and quaternary salts of the secondary amino monomer, in which:

R[1] is hydrogen, alkyl of 2 to 8 carbon atoms, an A monomer, or a B monomer; each of $R^2$ and $R^3$, taken independently of the other, is the same or different straight or branched chain alkanediyl group of the formula:

in which z has a value of from 2 to 8; $R^4$ is hydrogen satisfying one bond of the depicted geminally bonded carbon atom; and $R^5$ is hydrogen, alkyl of 2 to 8 carbon atoms, an A monomer, or a B monomer; $R^6$ is hydrogen, alkyl of 2 to 8 carbon atoms, an A monomer, or a B monomer; $R^7$ is a straight or branched chain alkanediyl group of the formula:

in which z has a value of from 2 to 8; and $R^8$ is hydrogen, alkyl of 2 to 8 carbon atoms, an A monomer, or a B monomer; and (b) at least one straight or branched nonionic hydrophilic segment A having from about 5 to about 1000 monomeric units which is defined above.

The polycationic segments in the copolymers of the invention can be branched. For example, polyspermine-based copolymers are branched. The cationic segment of these copolymers was synthesized by condensation of 1,4-dibromobutane and N-(3-aminopropyl)-1,3-propanediamine. This reaction yields highly branched polymer products with primary, secondary, and tertiary amines.

An example of branched polycations are products of the condensation reactions between polyamines containing at least 2 nitrogen atoms and alkyl halides containing at least 2 halide atoms (including bromide or chloride). In particular, the branched polycations are produced as a result of polycondensation. An example of this reaction is the reaction between N-(3-aminiopropyl)-1,3-propanediamine and 1,4-dibromobutane, producing polyspermine.

Another example of a branched polycation is polyethyleneimine represented by the formula:

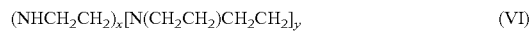

One example of useful polyamine-based copolymers is the polymer of formula:

in which:

F is a polyamine segment comprising a plurality of repeating units of formula —NH—R[0], wherein R[0] is an aliphatic group of 2 to 6 carbon atoms, which may be substituted;

G is polyethylene oxide or copolymer ethylene oxide and propylene oxide a straight or branched nonionic segment defined above;

$K^1$ and $K^2$ independently of the other, is hydrogen, hydroxy group, amonogroup, G or F polymer segments;

and each of $L^1$, $L^2$ and $L^3$, independently of the other, is a linking group or chemical bond.

The amino groups of polycationic segments can be quaternized to produce ammonium salts. Examples include polyspermine and polyamines that are modified with alkylhalides to produce tertiary and quaternized polyamines. Another useful type of cationic segments of well defined chemical structure are ionenes that can be aliphatic, heterocyclic or aromatic (Rembaum et al. *Polymer Letters,* 1968, 6:159; Tsutsui, T., Development in ionic polymers-2. Wilson, A. D. and Prosser, H. J. (eds.), Applied Science Publishers, London, N.Y. , vol. 2, pp. 163–187, 1986).

C. Anionic Copolymers.

Anionic copolymers contain at least one polyelectrolyte segment that yields a polyanion in an aqueous environment. This includes both strong polyacids having high ionization degrees in a broad range of pH, and weak polyacids characterized by pH-dependent ionization degrees. Anionic segments normally have a plurality of pendant amino groups such as carobxylic groups, sulfate groups, sulfonate groups, phosphate groups, and the like. Examples of anionic copolymers include but are not limited to polyoxyethylene-b-polymethacrylic acid (Wang, et al., *J. Polym. Sci.*, Part A: Polym. Chem., 30:2251, 1992), polystyrene-b-polyacrylic acid (Zhong, et al. *Macromolecules,* 25:7160, 1992), polyacrylic acid grafted with polyoxyethylene-b-polyoxypropylene-b-polyoxyethylene (Bromberg and Levin, *Macromol. Rapid Commun.* 17:169 1996).

D. Polypeptide Copolymers.

Polypeptide copolymers have a plurality of covalently bound polymer segments wherein the segments have at least one polypeptide segment and at least one non-peptide polymer segment. Polypeptide segments have a plurality of amino acid units or derivatives thereof.

Examples of useful segmented copolymers containing polypeptides include the poly(oxyethylene)-poly-L-lysine) diblock copolymer of the following formula:

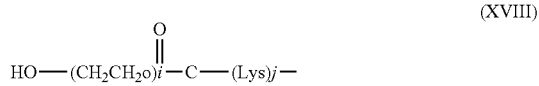

(XVIII)

wherein i is an integer of from about 2 to about 500, and j is an integer from about 4 to about 500 ((Lys)j is disclosed as SEQ ID NO: 42). A second example is the poly(oxyethylene)-poly-(L-alanine-L-lysine) diblock copolymer of formula:

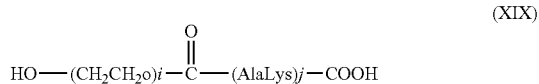

(XIX)

wherein i is an integer of from about 2 to about 500, and j is an integer from about 2 to about 500 ((AlaLys)j is disclosed as SEQ ID NO: 43).

The use of polypeptide copolymers in the invention allows for better control of the polypeptide segment lengths by using solid-phase and solution-phase chemistries. Segmented copolymers based on polypeptides with well defined chemical structures have been described in the literature, such as poly(amino acid)-β-poly(N,N-dietylacrylamide)-β-poly(amino acid) (Bromberg and Levin, *Bioconjugate Chem.* 9: 40, 1998). Further, the unit composition and sequence in polypeptides can be varied including hydrophobic, hydrophilic, ionizable, hydrogen and chemical bond forming amino acids and derivatives thereof to produce broader variability in the basis of the segmented copolymers.

E. Polynucleotide Copolymers.

Polynucleotide copolymers have a plurality of covalently bound polymer segments wherein the segments have at least one segment containing at least three nucleic acid units or the derivatives thereof. Similar to polypeptide copolymers, the polynucleotide copolymers provide for better control over segment length and sequence by using solid-phase and solution-phase chemistries. Segmented copolymers based on polynucleotides with well-defined chemical structure have been described including, polyoxyethylene-β-polynucleotide copolymer and polycation-β-polynucleotide copolymer (Vinogradov et al., *Bioconjugate Chemistry,* 7:3, 1996; U.S. Pat. No. 5,656,611). As with polypeptide copolymers, polynucleotide copolymers permit variation of the unit composition and sequence in polynucleotide segments which is particularly useful in selecting proper biological agent compositions pursuant to this invention.

VIII. Associating Biological Agents and Carriers with the Ligand

A. Conjugation of the Ligand

In another preferred embodiment the invention provides a Ligand of VEGF receptor, or derivative of the Ligand, conjugated to a therapeutic agent. Preferred therapeutic agents are described in the above description of invention.

In yet another preferred embodiment the invention provides a Ligand of VEGF receptor, or derivative of the Ligand, conjugated to a drug carrier system, such a carrier system being a polymer molecule, a block copolymer molecule, or a derivative of said polymer. The carrier system may also comprise a protein molecule. Preferred carrier systems are described in the above description of invention.

B. Methods of Chemical Conjugation.

The preparation of the conjugates of the Ligand to the therapeutic agent, or to the carrier system is effected by means of one of the known organic chemical methods for chemical ligation. The structural link between the Ligand and the macromolecule, as well as the chemical method by which they are joined, should be chosen so that the binding ability of the Ligand and the biological activity of the Ligand, when joined in the conjugate, are minimally compromised. As will be appreciated by those skilled in the art, there are a number of suitable chemical conjugation methods. The selection of the appropriate conjugation method can be rationalized by the inspection of the chemical groups present in the conjugated molecules, as well as evaluation of possible modification of these molecules to introduce some new chemical groups into them. Numerous chemical groups can subject conjugation reactions. The following groups are mentioned here as examples: hydroxyl group (—OH), primary and secondary amino group ($—NH_2$ and —NH—), carboxylic group (—COOH), sulfhydryl group (—SH), aromatic rings, sugar residues, aldehydes (—CHO), alphatic and aromatic halides, and others. Reactivity of these groups is well known in the art (Morrison and Boyd, Organic Chemistry, 6th Ed. (Prentice Hall, 1992), Jerry March, Advanced Organic Chemistry, $4^{th}$ Ed. (Wiley 1992), which are herein incorporated by reference). A more extensive description of conjugation methods and techniques can be found in: G. T. Harmanson, Bioconjugate Techniques, Academic Press, Inc. 1995, and in: S. S. Wong, Chemistry of Protein Conjugation and Cross-Linking, CRC Press, Inc. 1991, which are herein incorporated by reference.

C. Conjugation with Hydroxyl Group

Hydroxyl group —OH is present in peptides and proteins in side chains of serine, threonine, and tyrosine residues, and in sugar residues in sacharides and glycoproteins. Hydroxyl group is also present in many chemical compounds, including therapeutic agents such as paclitaxel, and in polymeric compounds, such as polisacherides and poloxamers. Hydroxyl groups exhibit nucleophilic properties and subject substitution reaction, for example alkylation (etherification), and acylation (esterification). The following reactive chemicals are preferred to conjugate with hydroxyls: alkyl halides (R—Cl, R—Br), cyanogen bromide (BrCN), acyl anhydrides, acyl halides, aldehydes (—CHO), hydrazides ($R—CO—NH—NH_2$), and others. Particularly preferred are: acyl anhydrides ($(R—CO)_2O$), and 1,1'-Carbonyldiimidazole (see: Anderson, G. W. and Paul, R., (1958) *J. Am. Chem. Soc.,* 80, 4423, which is herein incorporated by reference).

D. Conjugation with Amino Group

Amino group $—NH_2$ is present in peptides and proteins at their N-terminus, if these are not acylated, and in side chains of lysine residues. Amino group is also present in many chemical compounds, including therapeutic agents such as doxorubicin. Chemical and genetic methods allow for introduction of amino group into numerous other molecules, including peptides, proteins, small organic molecules and polymeric molecules. Amino group reveals nucleophile properties, and it subjects substitution reaction, for example alkylation, acylation, and condensation with aldehydes. The following reactive chemicals are preferred to conjugate with amines: alkyl halides (R—Cl, R—Br, R—I), aryl azides, acyl anhydrides, acyl halides, acyl esters, carboxylates activated with carbodiimides, aldehydes (—CHO), and others. Particularly preferred are: acyl anhydrides ((R—CO)$_2$O), acyl chlorides (R—CO—Cl), p-nitropheny esters (R—CO—O—C$_6$H$_4$—NO$_2$), N-hydroxysuccinimidyl esters (NHS esters, R—CO—O—N(CO—CH$_2$)$_2$), imidoesters (R—C(=NH)—O—CH$_3$), and carboxylic acids activated with carbodiimides (R—CO—OH+R'—N=C=N—R").

E. Conjuration with Sulfhydryl Group

Sulfhydryl group —SH is present in peptides and proteins containing cysteine residues. Sulfhydryl group is also present in many chemical compounds, and can be introduced into other compounds (see for example Carlsson, J., Drevin, H. and Axen, R. (1978) *Biochem. J.* 173, 723). Sulfhydryl group subjects elecrophilic substitution reaction, for example alkylation, and oxidation reaction. Preferred are the following reactive chemicals, useful to conjugate with —SH group: alkyl iodides, unsaturated acyls, and oxidizing agents. Particularly preferred are the following derivatives: iodoacetamides R—CO—CH$_2$—I, maleimides (R—N(CO—CH)$_2$), vinylsulfones (R—SO$_2$—CH=CH$_2$, Masri M. S. (1988). *J. Protein Chem.* 7, 49–54, which is herein incorporated by reference), didthiopyridyls (R—S—S-2-pyridyl).

F. Conjugation with Carboxyl Group

Carboxyl group —COOH is present in peptides and proteins at their C-terminus (if not amidated), and in side chains of aspartic acid and glutamic acid residues. Carboxyl group is also present in many chemical compounds, including therapeutic agents such as metotrexate. Chemical and genetic methods allow for introduction of carboxyl group into numerous other molecules, including peptides, proteins, small organic molecules and polymeric molecules. Carboxyl group is able to acylate nucleophilic groups, such as amines and hydroxyls. Carboxyl group requires activation prior to conjugation. The preferred methods of activation are: reaction with organic or inorganic acid halides (for example pivaloyl chloride, ethyl chloroformate, thionyl chloride, PCl$_5$), reaction with carbodiimides (R—CO—OH+R'—N=C=N—R", for example EDC, DCC), reaction with benzotriazolyl uronium or phosphonium salts (TBTU, BOP, PyBOP).

G. Conjugation with Cross-Linking Reagents

In preferred embodiment the conjugation of the Ligand of VEGF receptor to other molecules, either a therapeutic agent or a drug carrier molecule, is achieved with the support of cross-linking reagent. Particularly preferred are heterobifunctional cross-linking reagents. Variety of cross-linking regents is known to those skilled in the art (see, for example, S. S. Wong, Chemistry of Protein Conjugation and Cross-Linking, CRC Press, Inc. 1991. which are herein incorporated by reference).

Heterobifunctional reagents are particularly useful for linking two molecule, one of them having amino group, and the other having sulfhydryl group. In a preferred embodiment the Ligand of VEGF has a sulfhydryl group, and therefore is available for conjugation with variety of compounds bearing amino group. The following heterobifunctonal cross-linking reagents, for example, conjugate amino to sulfhydryl compounds: GMBS (N-[γ-Maleimidobutyryloxy]succinimide ester, Fujiwara, K., et al. (1988); *J. Immunol. Meth.* 112, 77–83)), SPDP (N-Succinimidyl 3-[2-pyridyldithio]propionate, Carlsson, J., et al. (1978). *Biochem.* *J.* 173, 723–737), SIA (N-Succinimidyl iodoacetate, Thorpe, P. E., et al. (1984). *Eur. J. Biochem* 140, 63–71.), SVSB (N-Succinimidyl-[4-vinylsulfonyl]benzoate).

Particularly preferred heterobifunctional linkers have polyoxyethylene chain between the two reactive groups. Coniugation with such likers yields products having hydrophilic junction between the two conjugated molecules, therefore it increases the solubility of the product in aqueous media. The following linkers with polyoxyethylene are mentioned here as examples: N-Maleimido-polyoxyethylene-succinimide ester (Sharewater Polymers, Cat. No. 2D2Z0F02), vinylsulfone-polyoxyethylene-succinimide ester (Shearewater Polymers, Inc. Al, Cat. No. 2Z5B0F02).

The said biological agents may be used in the invention as biologically active substances. They may as well be used as inactivated chemical derivatives of biological agents, i.e. prodrugs that are being converted to the active substances in certain physiological conditions by means of chemical or enzymatic modification of their structure. For example paclitaxel derivatives in which the 2' or 7-hydroxyl group is converted into an ester of a carboxylic acid form a prodrug (Deutsch et al., "Synthesis of congeners and prodrugs. 3. Water-soluble prodrugs of taxol with potent antitumor activity," *J. Med. Chem.*, 32:788–792, 1989.). For example doxorubicin derivative in which its amino group is acylated with a carboxylic group of amino acid derivative forms a prodrug (Breistol K, et al. "Superior therapeutic efficacy of N-L-leucyl-doxorubicin versus doxorubicin in human melanoma xenografts correlates with higher tumour concentrations of free drug." *Eur J Cancer.* 1999 July; 35(7):1143–9.; DeFeo-Jones D, et al. "A peptide-doxorubicin 'prodrug' activated by prostate-specific antigen selectively kills prostate tumor cells positive for prostate-specific antigen in vivo." *Nat. Med* 2000 November; 6(11):1248–52).

H. Genetical Fusion of Ligand with Therapeutic Polypeptides

In another embodiment of the invention, natural, modified, or recombinant nucleic acid sequences encoding the Ligand may be ligated to a biological active polypeptide sequence to encode a fusion protein. The general methods suitable for the construction and expression of Ligand fusions with therapeutic proteins are the same as those described herein above for recombinant production of Ligand. Chimeric Ligand-polypeptides may be most conveniently constructed by fusing in-frame the DNA sequence encoding the Ligand of present invention to a cDNA sequence encoding the polypeptide of interest. However, fusion to genomic fragments of therapeutic polypeptides can also be used. Alternatively, PCR techniques can be used to join the two parts of the molecule in-frame with an appropriate vector. Spacer of various length and structure can be inserted between the Ligand sequence and therapeutic protein in order to provide the fusion protein with additional flexibility and preserve the protein folding. The fusions of Ligand of the present invention can be purified by various well-known methods including affinity chromatography and immobilized metal chelate chromatography (Al-Mashikhi et al., *J. Dairy Sci.* 71:1756–1763 [1988]). Suitable fusion partners are as discussed in Section "Biological agents".

I. Introduction of Ligand in Virus Proteins

The Ligand of present invention can be introduced into viral particles in order to change a tropism of virus. Different viruses are capable of being used as vectors for the in vivo transfer and expression of genes. By way of example, retroviruses (RSV, HMS, MMS, and the like), HSV virus, adeno-associated viruses, adenoviruses, vaccinia virus, and the like, may be mentioned.

For example, the targeting of adenoviruses can be provided by construction of chimeric adenovirus fiber protein, which differs from the wild-type coat protein by the introduction of the Ligand amino acid sequence in a conformationally-restrained manner. Such a chimeric adenovirus fiber protein will be able to direct entry into cells of a vector comprising the chimeric fiber protein that is more efficient than entry into cells of a vector that is identical except for comprising a wild-type adenovirus fiber protein rather than the chimeric adenovirus fiber protein.

Desirably, the Ligand encoding sequence is introduced into the fiber protein at the level of gene expression. Such the Ligand amino acid sequence either is introduced in place of adenoviral sequences, or in addition to adenoviral sequences. Regardless of the nature of the introduction, its integration into an adenoviral fiber protein at the level of either DNA or protein, results in the generation of a SEQ ID NO:9 peptide motif in the chimeric fiber protein.

Redirecting viral vectors to VEGF receptor expressing tissues can be achieved by using bispesific conjugates produced by chemical linkage of anti-virus antibody to the Ligand of present invention, as described, for example for anti-adenovirus antibody (Haisma H J., et al., *Cancer Gene Ther.*, 2000, Alvarez R D., et al., *Clin. Cancer Res.*, 2000). To avoid the limitation of chemical conjugations, genetically fused proteins comprising of anti-fiber knob AB (or cellular adenovirus receptor, CAR) and the Ligand can be produced (Dmitriev I et al., *J. Virol.*, 2000).

The following examples are intended merely to illustrate the best mode now known for practicing the invention but the invention is not to be considered as limited to the details of such examples.

X. Application and Therapeutic Use

In another embodiment of the present invention provides a method of treating a disease associated with angiogenesis in a patient in need of such therapy comprising administering to the patient an effective amount of a pharmaceutical composition comprising at least one polypeptide or derivative thereof, wherein the polypeptide or derivative thereof is capable of specific binding with the high affinity VEGF receptor-1 or a derivative of the VEGF receptor-1 and structural similar receptors and a pharmaceutical acceptable carrier.

The angiogenesis mediated diseases include, but are not limited to, solid tumors; blood born tumors such as leukemias; tumor metastasis; benign tumors, for example hemangiomas, acoustic neuromas, neurofibromas, trachomas, and yogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation.

The Ligand is useful in the treatment of disease of excessive or abnormal stimulation of endothelial cells. These diseases include, but are not limited to, intestinal adhesions, Crohn's disease, atherosclerosis, scleroderma, and hypertrophic scars, i.e., keloids. The Ligand can be used as a birth control agent by preventing vascularization required for embryo implantation. The Ligand is useful in the treatment of diseases that have angiogenesis as a pathologic consequence such as cat scratch disease (Rochele minalia quintosa) and ulcers (*Helicobacter pylori*).

It should be understood that in addition to the ingredients, particularly mentioned above, the formulations of the present invention may include other agents conventional in the art having regard to the type of formulation in question, for example, those suitable for oral administration may include flavoring agents.

Diseases associated with corneal neovascularization that can be treated according to the present invention include but are not limited to, diabetic retinopathy, retinopathy of prematurity, corneal graft rejection, neovascular glaucoma and retrolental fibroplasia, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi's sarcoma, Mooren's ulcer, Terrien's marginal degeneration, mariginal keratolysis, trauma, rheumatoid arthritis, systemic lupus, polyarteritis, Wegener's sarcoidosis, scleritis, Stevens-Johnson disease, pemphigoid radial keratotomy, and corneal graph rejection.

Diseases associated with retinal/choroidal neovascularization that can be treated according to the present invention include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, Eales' disease, Behcet's disease, infections causing a retinitis or choroiditis, presumed ocular histoplasmosis, Bests disease, myopia, optic pits, Stargardt's disease, pars planitis, chronic retinal detachment, hyperviscosity syndromes, toxoplasmosis, trauma and post-laser complications. Other diseases include, but are not limited to, diseases associated with rubeosis (neovasculariation of the angle) and diseases caused by the abnormal proliferation of fibrovascular or fibrous tissue including all forms of proliferative vitreoretinopathy, whether or not associated with diabetes.

Diseases associated with chronic inflammation can be treated by the compositions and methods of the present invention. Diseases with symptoms of chronic inflammation include inflammatory bowel diseases such as Crohn's disease, ulcerative colitis, psoriasis, sarcoidosis and rheumatoid arthritis. Angiogenesis is a key element that these chronic inflammatory diseases have in common. The chronic inflammation depends on continuous formation of capillary sprouts to maintain an influx of inflammatory cells. The influx and presence of the inflammatory cells produce granulomas and thus, maintains the chronic inflammatory state. Inhibition of angiogenesis by the compositions and methods of the present invention inhibit the formation of the granulomas and alleviate the disease.

The compositions and methods of the present invention can be used to treat patients with inflammatory bowel diseases such as Crohn's disease and ulcerative colitis. Both Crohn's disease and ulcerative colitis are characterized by chronic inflammation and angiogenesis at various sites in the gastrointestinal tract. Crohn's disease is characterized by chronic granulomatous inflammation throughout the gastrointestinal tract consisting of new capillary sprouts surrounded by a cylinder of inflammatory cells. Inhibition of angiogenesis by the compositions and methods of the present invention inhibits the formation of the sprouts and prevents the formation of granulomas.

Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea.

The inflammatory bowel diseases also show extraintestinal manifestations such as skin lesions. Such lesions are characterized by inflammation and angiogenesis and can occur at many sites other than the gastrointestinal tract. The compositions and methods of the present invention are also capable of treating these lesions by preventing the angiogenesis, thus reducing the influx of inflammatory cells and the lesion formation.

Sarcoidosis is another chronic inflammatory disease that is characterized as a multisystem granulomatous disorder. The granulomas of this disease may form anywhere in the body and thus the symptoms depend on the site of the granulomas and whether the disease active. The granulomas are created by the angiogenic capillary sprouts providing a constant supply of inflammatory cells.

The compositions and methods of the present invention can also treat the chronic inflammatory conditions associated with psoriasis. Psoriasis, a skin disease, is another chronic and recurrent disease that is characterized by papules and plaques of various sizes. Prevention of the formation of the new blood vessels necessary to maintain the characteristic lesions leads to relief from the symptoms.

Another disease, which can be treated according to the present invention is rheumatoid arthritis. Rheumatoid arthritis is a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Other diseases that can be treated according to the present invention are hemangiomas, Osler-Weber-Rendu disease, or hereditary hemorrhagic telangiectasia, solid or blood borne tumors and acquired immune deficiency syndrome. In particular, the invention is useful for treating cancers, including, but not limited to, those cancers exhibiting solid tumors, such as breast, lung, ovarian, testicular, and colon cancers This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims. The ligand of the present invention is useful in inhibiting the angiogenic function of target cells both in vitro and in vivo. The ligand of the present invention is particularly useful in inhibiting the angiogenic function of endothelial cells both in vitro and in vivo. Of particular interest is the prevention or inhibition of endothelial cell differentiation into capillary structures. The endothelial cells amenable to inhibition by the Ligand are present at several sites in a mammal and include but are not limited to dermis, epidermis, endometrium, retina, surgical sites, gastrointestinal tract, liver, kidney, reproductive system, skin, bone, muscle, endocrine system, brain, lymphoid system, central nervous system, respiratory system, umbilical cord, breast tissue, urinary tract and the like. The treatment of the present invention using the ligand is particularly useful in preventing or inhibiting angiogenesis by endothelial cells at sites of inflammation and tumorigenesis.

Angiogenesis associated with autoimmune diseases may be treated using Ligand. The autoimmune diseases include but are not limited to rheumatoid arthritis, systemic lupus erythematosus, thyroiditis, Goodpasture's syndrome, systemic vasculitis, scleroderma, Sjogren's syndrome, sarcoidosis, primary biliary cirrhosis and the like.

Angiogenesis associated with wound repair may also be treated using the ligand. Excessive scarring resulting from excess angiogenesis often occurs at sites of skin trauma or surgical sites. Administration of the ligand at the site is useful in preventing or inhibiting angiogenesis at the site to eliminate or lessen the scarring.

The ligand is also useful in methods of inhibiting angiogenesis at a site of tumorigenesis in an immunocompromised mammal. The ligand administered at such sites prevents or inhibits blood vessel formation at the site thereby inhibiting the development and growth of the tumor. Tumors which may be prevented or inhibited by preventing or inhibiting angiogenesis with the ligand include but are not limited to melanoma, metastases, adenocarcinoma, sarcomas, thymoma, lymphoma, lung tumors, liver tumors, colon tumors, kidney tumors, non-Hodgkins lymphoma, Hodgkins lymphoma, leukemias, uterine tumors, breast tumors, prostate tumors, renal tumors, ovarian tumors, pancreatic tumors, brain tumors, testicular tumors, bone tumors, muscle tumors, tumors of the placenta, gastric tumors and the like.

In the method of treatment, the administration of the ligand, analogs, derivatives or fragments thereof may be for either "prophylactic" or "therapeutic" purpose. When provided prophylactically, the ligand is provided in advance of any symptom. The prophylactic administration of the ligand serves to prevent or inhibit any angiogenesis at a site. When provided therapeutically, the ligand is provided at (or after) the onset of a symptom or indication of angiogenesis. Thus, the ligand may be provided either prior to the anticipated angiogenesis at a site or after the angiogenesis has begun at a site.

It is proposed that the various compositions of the invention will be broadly applicable to the treatment or diagnosis of any tumor mass having a vascular endothelial component. Typical vascularized tumors are the solid tumors, particularly carcinomas, which require a vascular component for the provision of oxygen and nutrients. Exemplary solid tumors to which the present invention is directed include but are not limited to carcinomas of the lung, breast, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, neuroblastomas, and the like. The peptides of the present invention are useful in the treatment of various neoplastic and non-neoplastic diseases and disorders. Neoplasms and related conditions that are amenable to treatment include carcinomas of the breast, lung, esophagus, gastric anatomy, colon, rectum, liver, ovary, cervix, endometrium, thecomas, arrhenoblastomas, endometrial hyperplasia, endometriosis, fibrosarcomas, choriocarcinoma, head and neck cancer, nasopharyngeal carcinoma, laryngeal carcinoma, hepatoblastoma, Karposi's sarcoma, melanoma, skin carcinomas, hemangioma, cavernous hemangioma, hemangioblastoma, pancreas carcinoma, retinoblastoma, astrocytoma, glioblastoma, Schwannoma, oligodendroglioma, medulloblastorma, neuroblastomas, rhabdomyosarcoma, osteogenic sarcoma, leiomyosarcomas, urinary tract carcinomas, thyroid carcinomas, Wilm's tumor, renal cell carcinoma, prostate carcinoma, abnormal vascular proliferation associated with phakomatoses, edema (such as associated with brain tumors), and Meigs' syndrome.

Non-neoplastic conditions that are amenable to treatment include rheumatoid arthritis, psoriasis, atherosclerosis, diabetic and other retinopathies, retrolentral fibroplasia, neovascular glaucoma, age-related macular degeneration, thyroid hyperplasias (including grave's disease), corneal and other tissue transplantation, chronic inflammation, lung inflammation, nephrotic syndrome, preclampasia, ascites, pericardial effusion (such as associated with pericarditis) and pleural effusion. The following examples are intended merely to illustrate the best mode now known for practicing the invention but the invention is not to be considered as limited to the details of such examples.

IX. Methods of Use

The ligand compositions of the invention can be administered orally, topically, rectally, vaginally, by pulmonary route by use of an aerosol, or parenterally, i.e. intramuscularly, subcutaneously, intraperitoneallly or intravenously. The ligand composition can be administered alone, or it can be combined with a pharmaceutically-acceptable carrier or excipient according to standard pharmaceutical practice. For the oral mode of administration, the ligand compositions can be used in the form of tablets, capsules, lozenges, troches, powders, syrups, elixirs, aqueous solutions and suspensions, and the like. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the polynucleotide compositions can be combined with emulsifying and suspending agents. If desired, certain sweetening and/or flavoring agents can be added. For parenteral administration, sterile solutions of the conjugate are usually prepared, and the pH of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. For pulmonary administration, diluents and/or carriers will be selected to be appropriate to allow the formation of an aerosol.

The following examples will serve to further typify the nature of the invention but should not be construed as a limitation on the scope thereof, which is defined solely by the appended claims.

EXAMPLES

Example 1

```
Solid Phase Peptide Synthesis of the peptides:

H-Asn-Gly-Tyr-Glu-Ile-Glu-Trp-Tyr-Ser-Trp-Val-Thr-His-Gly-Met-Tyr-NH₂,           (SEQ ID NO: 1)

H-Cys-Asn-Gly-Tyr-Glu-Ile-Glu-Trp-Tyr-Ser-Trp-Val-Thr-His-Gly-Met-Tyr-NH₂,       (SEQ ID NO: 2)

Ac-Cys-Asn-Gly-Tyr-Glu-Ile-Glu-Trp-Tyr-Ser-Trp-Val-Thr-His-Gly-Met-Tyr-NH₂,      (SEQ ID NO: 3)

Fam-Asn-Gly-Tyr-Glu-Ile-Glu-Trp-Tyr-Ser-Trp-Val-Thr-His-Gly-Met-Tyr-NH₂,         (SEQ ID NO: 4)

Fam-Glu-Glu-Glu-Asn-Gly-Tyr-Glu-Ile-Glu-Trp-Tyr-Ser-Trp-Val-Thr-His-Gly-Met-Tyr-NH₂,  (SEQ ID NO: 5)

Fam-Asn-Gly-Tyr-Ile-Glu-Trp-Tyr-Ser-Trp-Val-Thr-His-Gly-Met-Tyr-NH₂.             (SEQ ID NO: 6)
```

For each synthesis the starting material was 0.6 g (0.4 mmol) of Rink Amide resin (4-(2',4'-Dimethoxyphenyl-Fmoc-aminomethyl)-phenoxy resin) substituted at a level of 0.66 mEq per gram of resin (Nova Biochem, Calif.). Each of the L-amino acids, starting with C-terminal tyrosine, was added in sequence in a synthesis cycle consisting of the three steps: of: piperidine deprotection (step 1), coupling (step 2) and ninhydrine test (step 3). If the test showed incomplete coupling, the coupling step was repeated. The synthesis of peptide SEQ ID NO: 2 was completed with additional Fmoc-deprotection (step 1). The synthesis of peptide SEQ ID NO: 3 was completed with Fmoc-deprotection (step 1), and acetylation (step 4). The synthesis of peptide SEQ ID NO: 4 was completed with Fmoc-deprotection (step 1), and labeling with fluoresceine (step 5). All the completed peptides were subjected to trifluoroacetic acid cleavage (step 6) and then purified (step 7). All the operations were performed in a glass reactor with a glass frit for draining the solvent. The resin was agitated with the solvents and the respective solutions using a shaker rotating the reactor for 180 degree.

1. Fmoc-Deprotection

The Fmoc-protecting group was removed from the starting resin, or from the ƒ-amino nitrogen of the amino acid previously attached to the resin, by treating the resin twice with 20% piperidine in dimethylformamide (DMF) (20 mL) for 3 min, and for 17 min. The resin was then washed six times with 10 mL of DMF, each wash taking one minute.

2. Coupling

The appropriate Fmoc-protected amino acid (2.4 mmol dissolved in 7 mL DMF), benzotriazole-1-yl-oxy-tris-pyrrolidino-phosphonium hexafluorophosphate (PyBOP) (1.25 g dissolved in 3 mL DMF), and diisopropylethylamine (0.84 mL) was added to the resin, and the mixture was agitated for 90 minutes. The resin was washed four times with 10 mL DMF. The amino acid derivatives used are represented in Table 1.

TABLE 1

| Amino Acid | Derivative |
|---|---|
| Tyr | Fmoc-Tyr(tBu)-OH |
| Met | Fmoc-Met-OH |
| Gly | Fmoc-Gly-OH |
| His | Fmoc-His(Trt)-OH |
| Thr | Fmoc-Thr(tBu)-OH |
| Val | Fmoc-Val-OH |
| Trp | Fmoc-Trp(Boc)-OH |
| Ser | Fmoc-Ser(tBu)-OH |
| Glu | Fmoc-Glu(OtBu)-OH |
| Ile | Fmoc-Ile-OH |
| Asn | Fmoc-Asn(Trt)-OH |
| Cys | Fmoc-Cys(Trt)-OH |

3. Ninhydrine Test

A small sample of the resin (approxymatly 30 beads) was transferred to a test tube. One drop of 1% ninhydrin solution in ethanol, one drop of 80% aqueous phenol, and one drop of 0.001% KCN in pyridine were added to the sample of resin, and the mixture was heated to 120° C. for 5 min. Blue color of beads showed incomplete coupling. In this case the coupling step 2 was repeated. If complete, the synthesis proceeded to the next cycle.

4. Acetylation of the Peptide SEQ ID NO: 3

After completion of the last cycle with Asn, and Fmoc-deprotection, the resin was agitated with acetic anhydride (0.22 mL) and diisopropylethylamine (0.84 mL) in 5 mL DMF for 90 minutes at room temperature.

5. Labeling of the Peptide SEQ ID NO: 4, SEQ ID NO: 5, and SEQ ID NO: 6 with Fluorescein After completion of the last cycle with Asn, and Fmoc-deprotection, the resin was agitated with 5(and 6-)-carboxy-fluorescein (0.9 g dissolved in 5 mL DMF), PyBOP (1.25 g dissolved in 3 mL DMF), and diisopropylethylamine (0.84 mL) for 120 min.

6. Cleavage with Trifluoroacetic Acid

The resin was washed 6 times with DMF, twice with DMF/methanol (1:1 v/v), and three times with methanol, and dried in vacuum for 1 hour. A mixture of trifluoroacetic acid (TFA, 9 mL), water (0.5 mL), ethanedithiol (0.25 mL) and triisopropylsilane (0.25 mL) was added to the dry resin, and was agitated for 2 hours. The liquid was drained, and the resin was washed with 2 mL TFA. Combined liquids were evaporated in a stream of dry nitrogen. The residue was washed twice with 20 mL of anhydrous ether, and the peptide was extracted with a 1:1 mixture of $CH_3COOH:H_2O$ (20 mL), and freeze dried.

7. Purification

The lyophilized powder was dissolved in a mixture $CH_3CN:H_2O$ (1:1, V/V, 10 mg of crude peptide in 2 mL) and loaded onto a Vydac C18 preparative column (25×2.25 cm). The loaded column was eluted with a two-component eluent, 60% of solution A in solution B, at flow rate 5 mL/min. Solution A was 0.1% TFA in $H_2O$, and solution B was 0.1% TFA in $CH_3CN$. Fractions were identified by electro-spray MS. Fractions exhibiting purity equal to or better than that desired were pooled and lyophilized. The product was dissolved in $CH_3COOH:H_2O$ (1:1, v/v, 1 mL per 1 mg of product) to render the purified final product as the acetate salt. The products of the peptide synthesis are shown in Table 2.

TABLE 2

| SEQ ID NO: | Yield [mg] | m/e (double charge) |
|---|---|---|
| 1 | 28 | 1017.4 |
| 2 | 24 | 1069.2 |
| 3 | 20 | 1091.0 |
| 4 | 7 | 1195.3 |
| 5 | 2 | 1391.0 |
| 6 | 10 | 1132.7 |

Example 2

Conjugation of peptides with carrier protein The compounds of the invention are tested for their ability to bind VEGF receptor after chemical conjugation to the carrier protein.

The carrier protein, for example horseradish peroxidase (ICN, 250 u/mg) was dissolved in phosphate buffer (0.1M Na2HPO4, 0.1M NaCl, 1 mM EDTA and pH 8.5) at final concentration 3 mg/ml. N-succinimidyl-3-(2-pyridylthio) propionate (SPDP, Sigma Chemical) was dissolved in 133, ul of dimethylformamide (DMFA), in a proportion of 0.234 mg SPDP=39 ul DMFA. The solution of SPDP was added to solution of peroxidase and incubated with stirring at room temperature for 30 minutes. After modification, activated protein was purified by gel filtration. The solution of peroxidase was applied to the Sephadex G-25 column (Fisher, 20 ml) and eluted with 50 ml of phosphate buffer. Detect at 280nm with a sensitivity of 50 and lamp intensity of 0.005 Au. The fractions (1 ml) were collected using a fraction collector (Pharmacia Biotech). The fractions containing modified Peroxidase were selected and combined (total volume of 5–7 ml). Aliquot of 1 ml was kept for the control. Number of activated groups was evaluated by treatment of aliquot of activated protein with 1 mg/ml of L-cysteine methyl ester hydrochloride (Aldrich Chemical). Amount of recovered 2-pyridyl disulphide was measured by UV absorbency at 343 nm. Control sample was treated with cysteine for 15 hours at room temperature, purified by gel filtration and used as a reference in receptor binding assays, which are described in Example 15. The peptide (SEQ ID NO: 2), 1 mg was dissolved in 200 μl of phosphate buffer. Activated peroxidase was mixed with the peptide and incubated with stirring for 24 hours, at room temperature. The reaction was controlled by UV detection at 343 nm (detection of 2-pyridyl disulphide). The conjugate was purified by gel filtration using Sephadex G-25 column. The conjugate fractions were collected and combined. The protein concentration was determined using Bradford method (Coomasie blue, Bio-Rad) and conjugation was confirmed by SDS/PAAG electrophoresis. Peroxidase activity of the conjugate (Conjugate NO 1) per mg of protein was determined by incubation of conjugate aliquots with ABTS solution (0.22 mg/ml 2'2'-azino-bis-93'-ethylbenzthiazoline-6-sulphonic acid) diammonium salt, 0.05M citric acid, pH 4.0, 0.05% $H_2O_2$) for 30 min. at room temperature and detection the absorbance at A405.

Example 3

Synthesis of CONJUGATE NO.: 2 (PEG1500-peptide (SEQ ID NO: 3))

The conjugates ID NO 2 was prepared using di-amino derivative of polyoxyethylene MW 1500 (PEG-bis-amine MW 1500 from Shearwater Polymers, Inc. Al., Cat. No.

PT-017-08). PEG-bis-amine was reacted, with SPDP (N-Succinimidyl 3-[2-pyridyldithio]propionate, from Sigma, Cat. No. P-3415) (step 1). The resulting PEG-bis-SS-pyridyl was purified with HPLC, and it was reacted with excess of peptide SEQ ID NO: 3 (step 2). The progress of the conjugation reaction was monitored by light UV absorption at 340 nm. Upon completion, the components of the reaction mixture were separated using HPLC.

1. Conjugation of PEG-bis-amine with SPDP.

PEG-bis-amine (15 mg dissolved in 0.2 mL methanol) was mixed with SPDP (5 mg dissolved in 0.1 mL methanol) and diisopropylethylamine (0.027 mL of 10% solution in methanol). The mixture was stirred for 30 minutes, and then it was loaded onto a Vydac C18 preparative column (25× 2.25 cm). The column was eluted with a two-component eluent gradient 0.5% per minute, starting from 0% of solution B in solution A, at flow rate 5 mL/min. Solution A was 0.1% TFA in $H_2O$, and solution B was 0.1% TFA in $CH_3CN$. Fractions were identified by electrospray MS, and by increased UV absorption at 340 nm after mixing sample with 1% ethanedithiol in methanol (1:1 v/v). Fractions 50–60 mL after the void volume were pooled together and freeze dried, and yield 6.3 mg of PEG-bis-SS-pyridyl.

2. Conjugation of PEG-bis-pyridyl with Peptide SEQ ID NO: 3.

PEG-bis-pyridyl (2 mg dissolved in 1 mL water) was mixed with peptide SEQ ID NO: 3 (6 mg dissolved in 0.1 mL methanol). The mixture was stirred and its UV absorbance at 340 nm was monitored. After 24 hrs the mixture was loaded onto a Vydac C18 preparative column (25×2.25 cm). The column was eluted with a two-component eluent gradient 0.5% per minute, starting from 0% of solution B in solution A, at flow rate 5 mL/min. Solution A was 0.1% TFA in $H_2O$, and solution B was 0.1% TFA in $CH_3CN$. Fractions 110–120 mL after the void volume were pooled together and freeze dried, and yield 1.1 mg of CONJUGATE NO.: 2 (PEG 1500-peptide (SEQ ID NO: 3)).

Example 4

Synthesis CONJUGATE NO.: 3 (polylysine-PEG1500-peptide (SEQ ID NO: 3))

The conjugates ID NO 3 was prepared using di-amino derivative of polyoxyethylene MW 1500 (PEG-bis-amine MW 1500 from Shearwater Polymers, Inc. Al., Cat. No. PT-017-08). PEG-bis-amine was reacted, with SPDP (N-Succinimidyl 3-[2-pyridyldithio]propionate, from Sigma, Cat. No. P-3415), and the resulting PEG-bis-SS-pyridyl was purified with HPLC, (step 1). Polylysine $(H-Lys)_8(H-Lys)_4(Lys)_2LysCysNH_2$ (SEQ ID NO: 38) was synthesized according to the protocols described in Example 1 (step 2). Peptide SEQ ID NO: 3 was reacted with excess of PEG-bis-SS-pyridyl, followed by adding of an excess of polylysine to the reaction (step 3). The progress of the conjugation reaction was monitored by light UV absorption at 340 nm. Upon completion, the components of the reaction mixture were separated using HPLC.

1. Conjugation of PEG-bis-amine with SPDP.

PEG-bis-amine (15 mg dissolved in 0.2 mL methanol) was mixed with SPDP (5 mg dissolved in 0.1 mL methanol) and diisopropylethylamine (0.027 mL of 10% solution in methanol). The mixture was stirred for 30 minutes, and then it was loaded onto a Vydac C18 preparative column (25× 2.25 cm). The column was eluted with a two-component eluent gradient 0.5% per minute, starting from 0% of solution B in solution A, at flow rate 5 mL/min. Solution A was 0.1% TFA in $H_2O$, and solution B was 0.1% TFA in $CH_3CN$. Fractions were identified by electrospray MS, and by increased UV absorption at 340 nm after mixing sample with 1% ethanedithiol in methanol (1:1 v/v). Fractions 50–60 mL after the void volume were pooled together and freeze dried, and yield 6.3 mg of PEG-bis-SS-pyridyl.

2. Solid Phase Synthesis of Polylysine $(H-Lys)_8(H-Lys)_4(Lys)_2LysCysNH_2$ (SEQ ID NO: 38)

The synthesis of polylysine was performed using 0.5 g (0.1 mmol) of NovaSyn TGR resin (Nova Biochem, Cat. No. 01-64-0060), using Fmoc-Cys(TRT)-OH for the first cycle of the synthesis, and Fmoc-Lys(Fmoc)-OH for next four synthetic cycles. Each synthetic cycle consisted of steps 1–3 of the Example 1. The reaction was completed with Fmoc-deprotection (step 1 of the Example 1), and cleavage (step 6 of the Example 1). The product was purified on HPLC using Vydac C18 preparative column (25×2.25 cm). The column was eluted with a two-component eluent gradient 0.5% per minute, starting from 0% of solution B in solution A, at flow rate 5 mL/min. Solution A was 0.1% TFA in $H_2O$, and solution B was 0.1% TFA in $CH_3CN$. Fractions were identified by electrospray MS, and by dark blue color developed after mixing sample with 1% ninhydrin in butanol (1:1 v/v) at 120° C. for 1 min. The yield of freeze-dried product (polylysine) was 21 mg.

3. Conjugation of PEG-bis-pyridyl with Peptide SEQ ID NO: 3.

PEG-bis-pyridyl (3 mg dissolved in 1 mL water) was mixed with peptide SEQ ID NO: 3 (1 mg dissolved in 0.1 mL methanol). UV absorbance of the mixture at 340 nm was monitored. After 24 hrs polylysine was added (6 mg dissolved in 0.1 mL water). UV absorbance of the mixture at 340 nm was further monitored. The mixture was stirred for 72 hrs, and then it was loaded onto a Vydac C18 preparative column (25×2.25 cm). The column was eluted with a two-component eluent gradient 0.5% per minute, starting from 0% of solution B in solution A, at flow rate 5 mL/min. Solution A was 0.1% TFA in $H_2O$, and solution B was 0.1% TFA in $CH_3CN$. Fractions were identified by dark blue color developed after mixing sample with 1% ninhydrin in butanol (1:1 v/v) at 120° C. for 1 min. Fractions 20–30 mL after the void volume were pooled together and freeze dried, and yield I mg of CONJUGATE NO.: 3 (polylysine-PEG1500-peptide (SEQ ID NO: 3)).

Example 5

Synthesis of CONJUGATE NO.: 4 (PEI-PEG-peptide (SEQ ID NO: 3))

PEI-PEG conjugate was prepared from polyethyleneimine MW ca. 2000 (PEI) and polyethylene glycol MW ca. 8000 (PEG) using carbonyldiimidazol (CDI) as previously described in Kabanov, A. V et al., *Bioconjugate Chemistry* 6, 639–643, 1995. PEI-PEG conjugate (10 mg dissolved in 0.2 mL phosphate buffer pH 8) was mixed with SPDP (3 mg from Sigma, dissolved in 0.05 mL dimethylformamide,) for 30 minutes. Then the mixture was applied onto a Sephadex G-25 column (Fisher, 20 ml) and eluted with 50 ml of phosphate buffer, and detect with UV absorption at 280 nm. The fraction containing PEI-PEG modified with SS-pyridyl was identified by increased UV absorption at 340 nm after mixing a sample with 1% ethanedithiol in methanol (1:1 v/v). This fraction (2 mL) was mixed with peptide SEQ ID NO: 3 (5 mg dissolved in 0.05 mL DMF), and was stirred for 18 hrs. UV absorbance of the mixture at 340 nm was monitored. Acetic anhydride (0.005 mL) was added to the mixture, and it was stirred for 3 hrs. Then the mixture was dialyzed through cellulose membrane (Spectra/Por 1, MWCO 6000–8000) against water for 48 hrs. Finally, freeze-drying yielded 4.5 mg of the product.

Example 6

Synthesis of CONJUGATE NO.: 5 (paclitaxel-PEG-peptide (SEQ ID NO: 3))

Peptide SEQ ID NO: 2 was conjugated with Fmoc-NH-PEG-COO—N-succinimidyl (MW 3400 from Shearwater Polymers, Inc. Al., Cat. No. 1P2Z0F02), followed by Fmoc group removal with piperidin (step 1). The product was purified by HPLC. Paclitaxel-2'-succinate was obtained by the method described by Deutsch H. M. et al. (1989), *J. Med. Chem.* 32, 788–792. Paclitaxel-2'-succinate was conjugated with NH-PEG-peptide (SEQ ID NO: 2) by means of EEDQ (2-ethoxy-1-ethoxycarbonyl-1,2-dihydroquinoline, the method was described by Safavy A. et al. (1999) *J. Med. Chem.* 42, 4919–4924), and produced CONJUGATE NO.: 5 (paclitaxel-PEG-peptide (SEQ ID NO: 3)) (step 2).

1. Synthesis of amino-PEG-peptide (SEQ ID NO: 2)

Peptide SEQ ID NO: 2 (5 mg dissolved in 2 mL methanol) was mixed with Fmoc-NH-PEG-COO—N-succinimidyl (15 mg dissolved in 1 mL methanol) and diisopropylethylamine (0.01 mL of 10% solution in methanol). The mixture was stirred for 120 minutes, and then the solvent was removed in vacuum. The residue was dissolved in piperidine (1 mL of 20% solution in dimethylformamide), and it was mixed for 20 minutes. The mixture was then condensed in vacuum to 0.3 mL, and was diluted with 1 mL 50% aqueous acetonitrile, and it was loaded onto a Vydac C18 preparative column (25×2.25 cm). The column was eluted with a two-component eluent gradient 0.5% per minute, starting from 10% of solution B in solution A, at flow rate 5 mL/min. Solution A was 0.1% TFA in $H_2O$, and solution B was 0.1% TFA in $CH_3CN$. Fractions were identified by electrospray MS. Fractions 60–80 mL after the void volume were pooled together and freeze dried, and yielded 3 mg of amino-PEG-peptide (SEQ ID NO: 2).

2. Synthesis of CONJUGATE NO.: 5 (paclitaxel-PEG-peptide (SEQ ID NO: 3)

Paclitaxel-2'-succinate (2 mg dissolved in 0.2 mL dimethylformamide) and EEDQ (1 mg) were mixed for 30 minutes. Then amino-PEG-peptide (SEQ ID NO: 2) (3 mg in 0.2 mL dimethylformamide) was added, and the mixture was stirred for 3 hrs. The product was purified on Vydac C18 preparative column (25×2.25 cm) by elution with a two-component eluent gradient 0.5% per minute, starting from 10% of solution B in solution A, at flow rate 5 mL/min. Solution A was 0.1% TFA in $H_2O$, and soution B was 0.1% TFA in $CH_3CN$. Fractions were identified by electro-spray MS. Fractions 90–100 mL after the void volume were pooled together and freeze dried, and yielded 1.2 mg of CONJUGATE NO.: 5 (paclitaxel-PEG-peptide (SEQ ID NO: 3)).

Example 7

Synthesis of CONJUGATE NO.: 6 (F127-peptide (SEQ ID NO: 3))

F127-bis-amine, amino derivative of block copolymer polyoxyethylene-polyoxypropylene-polyoxyethylene (pluronic F127 from BASF, MW 12600) was prepared using carbonyldiimidazol (CDI) and aqueous ammonium (step 1). F127-bis-amine was modified with SPDP heterobifunctional linker to produce F127-bis-SS-pyridyl (step 2). The conjugate ID NO 6 (F127-peptide (SEQ ID NO: 3)) was then prepared by reaction of F127-bis-SS-pyridyl with peptide SEQ ID NO: 3 (step 3).

1. Synthesis of polyoxyethylene-polyoxypropylene-polyoxyethylene-bis-amine (F127-bis-amine)

Pluronic F127 (100 mg dissolved in 3 mL acetonitrile) and carbonyldiimidazol (26 mg) were mixed for 16 hrs. Then 0.05 mL of conc. aqueous ammonium was added, and the mixing continued for 24 hrs. The volatile components were removed in vacuum. The solid residue was dissolved in 10 mL 1-buthanol and extracted 10 times with 5 mL 1% sulfuric acid in 15% aqueous sodium chloride, 3 times with 1% sodium bicarbonate in 15% aqueous sodium chloride, and 3 times with 20% aqueous sodium chloride. Finally, the organic phase was evaporated, the residue was dissolved in water and freeze-dried. The product (70 mg) was analyzed by thin layer chromatography (TLC), and showed a single spot on silica gel plates (Siloca gel 60, Riede-de Haen) developed with chloroform-methanol (7:3 v/v), and visualized with ninhydrine, and with iodine.

2. Synthesis of F127-bis-SS-pyridyl

F127-bis-amine (15 mg dissolved in 0.2 mL methanol) was mixed with SPDP (5 mg dissolved in 0.1 mL methanol) and diisopropylethylamine (0.027 mL of 10% solution in methanol). The mixture was stirred for 30 minutes, and then evaporated. The residue was dissolved in 2 mL of 1-butanol and extracted 3 times with 1 mL 1% sulfuric acid in 15% aqueous sodium chloride, 6 times with 1% sodium bicarbonate in 15% aqueous sodium chloride, and 3 times with 20% aqueous sodium chloride. Then, the organic phase was evaporated, the residue was dissolved in anhydrous ethanol, and filtered. The ethanol solution was dried, redissolved in water and freeze-dried. The product (10 mg) was analyzed by thin layer chromatography (TLC), and showed a single spot on silica gel plates developed with chloroform-methanol (6:4 v/v), visualized with iodine, and not with ninhydrine.

3. Synthesis of Conjugate No.: 6 (F127-peptide (SEQ ID NO: 3))

F127-bis-SS-pyridyl (10 mg dissolved in 1 mL phosphate buffer pH 8) was mixed with peptide SEQ ID NO: 3 (2 mg dissolved in 0.02 mL DMF), and was stirred for 18 hrs. UV absorbance of the mixture at 340 nm was monitored. Then the mixture was dialysed through cellulose membrane (Spectra/Por 1, MWCO 6000–8000) against water for 48 hrs. Freeze-drying yield 8 mg of the product.

Example 8

Synthesis of CONJUGATE NO.: 7 (paclitaxel-polyglutamic acid-peptide (SEQ ID NO: 1))

Paclitaxel-polyglutamic acid (paclitaxel-PG) was prepared from polyglutamic acid (PG) and paclitaxel using dicyclohexylcarbodiimide (DCC) in dimethylformamide. Paclitaxel-polyglutamnic acid-peptide (SEQ ID NO: 1) (CONJUGATE. NO.: 7) was prepared from paclitaxel-PG and peptide (SEQ ID NO: 1) also using dicyclohexylcarbodiimide in dimethylformamide.

1. Synthesis of paclitaxel-polyglutainic Acid

Polyglutamic acid sodium salt (MW 50 K, Sigma, 0.5 g) was dissolved in water. The pH of the aqueous solution was adjusted to 2 using 0.2 M HCl. The precipitate was collected, dialyzed against distilled water, and lyophilized to yield 0.44 g PG. To a solution of polyglutamic acid (100 mg, 0.6 mmol of Glu residues) in anhydrous dimethylformamide (2 mL) was added paclitaxel (10 mg, 0.011 mmol), dicyclohexyl-carbodimide (5 mg, 0.025 mmol) and dimethylaminopyridine (0.1 mg). The reaction was allowed to proceed at room temperature for 12 hrs. The reaction was controlled by thin layer chromatography on silica gel plates, using chlorophormlMeOH (10:1) After 12 hours chromatography showed complete conversion of paclitaxel (Rf=0.5) to polymer conjugate (Rf=0). The reaction mixture was poured into chloroform. The precipitate was collected and dried in vacuum, dissolved in distilled water and freeze-dried to yield 0.1 g of paclitaxel-polyglutamic acid.

2. Synthesis of paclitaxel-polyglutanmc acid-peptide (SEQ ID NO: 1)

Paclitaxel-polyglutamic acid (0.1 g) was dissolved in anhydrous dimethylformamide (2 mL), and dicyclohexyl-carbodiimide (3 mg) was added, and stirred gently for 5 minutes. Then peptide (SEQ ID NO: 1) (3 mg) was added, and stirred for 12 hours. The reaction mixture was poured into chloroform. The precipitate was collected and dried in vacuum, dissolved in distilled water and freeze-dried to yield 0.1 g of paclitaxel-polyglutamic acid-peptide (SEQ ID NO: 1).

Example 9

Synthesis of CONJUGATE NO.: 8 (paclitaxel-peptide (SEQ ID NO: 1))

Paclitaxel-2'-succinate was obtained by the method described by Deutsch H. M. et al. (1989), *J. Med. Chem.* 32, 788–792. Paclitaxel-2'-succinate was conjugated with peptide (SEQ ID NO: 1) by means of EEDQ (2-ethoxy-1-ethoxycarbonyl-1,2-dihydroquinoline, the method was described for example by Safavy A. et al. (1999) *J. Med. Chem.* 42, 4919–4924), and produced CONJUGATE ID NO 8 (paclitaxel-peptide(SEQ ID NO: 1)). The product was purified by HPLC.

Paclitaxel-2'-succinate (2mg dissolved in 0.2 mL dimethylformamide) and EEDQ (1 mg) were mixed for 30 minutes. Then peptide (SEQ ID NO: 1) (3 mg in 0.2 mL dimethylformamide) was added, and the mixture was stirred for 3 hrs. The product was purified on Vydac C18 preparative column (25×2.25 cm) by elution with a two-component eluent gradient 0.5% per minute, starting from 10% of solution B in solution A, at flow rate 5 mL/min. Solution A was 0.1% TFA in H$_2$O, and solution B was 0.1% TFA in CH$_3$CN. Fractions were identified by electro-spray MS (m/z 1485.4 double charged).

Example 10

Synthesis of CONJUGATE ID. NO.: 9 (peptide (SEQ ID NO: 3)-Leucyl-doxorubicin)

1. Modification of Leucyl-doxorubicin

Leucyl-doxorubicin was modified using the heterobifunctional linker SPDP to produce pyridyl-SS-propionylleucyl-doxorubicin (step 1). The conjugate ID NO 9 (peptide (SEQ ID NO: 3)-Leucyl-doxorubicin) was then prepared by reaction of pyridyl-SS-propionylleucyl-doxorubicin with peptide SEQ ID NO: 3 (step 2).

Solution of L-leucyl-doxorubicin (6 mg, 0.01 mmol) in 0.1 mL mathanol was mixed with SPDP (3 mg) solution in 0.1 mL methanol, and diisropylethylamine (0.015 mL of 10% solution in methanol). The mixture was stirred for 20 minutes. The mixture was fractionated using reverse phase HPLC with water—acetonitrile gradient (1% per minute, starting from 10% acetonitrile). The fractions containing the product pyridyl-SS-propionylleucyl-doxorubicin were identified by MS (m/z 854).

2. Purification

Pyridyl-SS-propionylleucyl-doxorubicin (1 mg dissolved in 0.1 mL dimethylformamide) was mixed with peptide SEQ ID NO: 3 (2 mg dissolved in 0.02 mL DMF), and was stirred for 18 hrs. The mixture was diluted with 2 mL water and freeze dried. The remaining material was purified with using reverse phase HPLC with water—acetonitrile gradient (1% per minute, starting from 10% acetonitrile). The fractions containing the product (peptide (SEQ ID NO: 3)-Leucyl-doxorubicin) (CONJUGATE NO.:9) were identified by MS (m/z 1440.5 double charged).

Example 11

Synthesis of the Radioactive Labeled Peptide [3HC]—CO-Cys-Asn-Gly-Tyr-Glu-Ile-Glu-Trp-Tyr-Ser-Trp-Val-Thr-His-Gly-Met-Tyr-NH$_2$ (SEQ ID NO: 3)

The peptide SEQ ID NO: 2 (2 mg) was dissolved in 0.1 mL of 100 mM solution of sodium bicarbonate. 0.0001 mL of [$^3$H]Acetic anhydride (4–10 Ci/mmol, from Amersham Pharmacia Biotech) was added, and the mixture was stirred for 15 minutes. Then the mixture was acidified with 0.1 mL of 200 mM acetic acid, and was applied on 1 mL C-18 solid phase extraction cartridge (Supelco Supelclean LC-18 SPE). The cartridge was washed with water (2 mL), and the product was eluted with mixture of water and acetonitrile (55:45 v/v), 2 mL. The eluted product showed radioactivity of 0.5 mCi.

Example 12

Peptide SEQ ID NO: 4 Partitioning in Formulation with Polyoxamer F127

The partitioning coefficient P describes the tendency of the peptide to stay formulated within micelles. $P=[x]_m/[x]_w$, where $[x]_m$ is the actual concentration of the substance x inside micelles, $[x]_w$ is the actual concentration of the substance x in aqueous phase. Partitioning of the peptide SEQ ID NO: 4 was determined in the formulation consisting of solution of pluronic F127 (BASF) in phosphate buffer saline (PBS, pH 7.5) using the fluorescence dependence method (Kabanov A. et al. (1995), *Macromolecules* 28. 2303–2314). A series of solutions of pluronic F127 (concentration ranging from 0.001% to 3% weight/weight) in PBS was used to dissolve the peptide SEQ ID NO: 4 to obtain the final concentration of 0.001 mM. The solutions (0.2 mL each) were incubated at 37° C. for 4 hrs in 96 well plate (transparent polystyren, flat bottom, from Sarstedt), and the fluorescence of the solution (excitation 485 nM, emission 530 nm) was measured using a plate reader FL600 (BioTek). The partitioning constant P was found by fitting the measured fluorescence values to the equation:

$$(I_{max}-I_0)/(I-I_0)-1=1/(\theta P)-1/P$$

where:

I—fluorescence $I_{max}$—fluorescence at maximum concentration of polymer $I_0$—fluorescence at minimum concentration of polymer P—partitioning constant ✓=0.01✓([F127]−CMC$_{F127}$), volume portion of the micellar phase ✓—partial specific volume of micelles, approximately ✓=0.8

[F127]—concentration of the polymer

CMC$_{F127}$=0.003% critical micelle concentration of polymer

The same procedure was also applied to fluorescein as a reference compound.

The results are represented in Table 3.

TABLE 3

| Substance | Partitioning in F127 |
|---|---|
| Peptide SEQ ID NO: 4 | 100 |
| Fluorescein | 40 |

Example 13

Partitioning of Pyren in Formulation with CONJUGATE NO.: 6 (F127-peptide (SEQ ID NO: 3))

The partitioning coefficient P describes the tendency of pyren, which is an example hydrophobic organic molecule, to stay formulated within micelles formed by the polymer mixture containing CONJUGATE ID NO 6. The polymer mixture used for the formulation consisted of pluronic F127 (BASF) and the CONJUGATE ID NO 6, 90:10 (weight/weight). Assuming the typical aggregation number for micelles 10–30, the formulation contains 2–6 peptide molecules per micelle. P=[x]$_m$/[x]$_w$, where [x]$_m$ is the actual concentration of pyren inside micelles, [x]$_w$ is the actual concentration of pyren in aqueous phase. The partitioning was determined using the fluorescence dependence method (Kabanov A. et al. (1995), *Macromolecules* 28. 2303–2314). A series of solutions of the polymer mixture (concentration from 0.001% to 3% weight/weight) in PBS pH 7.5 was used to dissolve pyren to obtain the final concentration of 0.0005 mM. The solutions (0.2 mL each) were incubated at 37° C. for 4 hrs in 96-well plate (quarz, Helma), and the fluorescence of the solution (excitation 340 nM, emission 400 nm) was measured using plate reader FL600 (BioTek). The fluorescence dependence on the concentration of polymer was analyzed, and the partitioning constant P was found by fitting the measured fluorescence values to the equation:

$(I_{max}-I_0)/(I-I_0)-1=1/(\theta P)-1/P,$ where:

I—fluorescence $I_{max}$—fluorescence at maximum concentration of polymer $I_0$—fluorescence at minimum concentration of polymer P—partitioning constant ✓=0.01✓([polymer]−CMC$_{polymer}$), volume portion of the micellar phase ✓—partial specific volume of micelles, approximately ✓=0.8

[polymer]—concentration of the polymer

CMC$_{polymer}$ critical micelle concentration of polymer; CMC of the mixture of F127 and CONJUGATE ID NO 6 was found to be 0.003%, the same as for pure F127.

The same procedure was also applied to formulation of pyren in pluronic F127 as a reference.

The results are represented in Table 4.

TABLE 4

| Polymer | CMC | Partitioning in F127 |
|---|---|---|
| F127 and CONJUGATE. NO.: 6 (9:1 w/w) | 0.003% | 1850 |
| F127 | 0.003% | 2000 |

Example 14

The Ability of Peptides to Bind the VEGF Receptor-1

The compositions of the invention are tested for the binding to immobilized VEGF receptor-1. To immobilize the VEGF receptor are used streptavidin-coated microtiter plates, preblocked with BSA (Boehringer Mannheim). Total binding capacity for biotin-labeled AB=1.5 µg/well. Biotin-labeled anti-human FC antibody (ICN) 10 µg/ml in 0.1% BSA/PBS are added into each well of streptavidin-coated plate (3 wells for each sample to be tested). The microtiter plates are incubated at 4° C. for 8 hours in a humidified container (e.g., a sealed container containing moistened paper towels). After incubation, the contents of microtiter wells is emptied by inverting plate and flicking the well contents into a suitable container, tapping the inverted plate on a paper towel to remove any liquid remaining in the wells. Then, microtiter plates are washed for 4 times with 300 µl of 0.1% BSA/PBS. Recombinant human Flt-1/Fc chimera (R&D Systems) is used as a source of VEGF receptor-1. The cDNA sequence for the endogenously encoded soluble human Flt-1, containing six IgG-like extracellular domains of Flt-1 receptor (Shibuya, M. et. al., 1990, *Oncogene* 5: 519–524; Kendall, R. L. and K. A. Thomas 1993, *Proc. Natl. Acad. Sci. USA* 90: 10705–10709) was fused to the Fc region of human IgG$_1$. The recombinant soluble Flt-1/Fc chimera binds VEGF and PlGF with high affinity according to supplier certificate. The Flt-1/Fc chimera (1 µg/100 µl in 0.1% BSA/PBS) is added into each well. Plates are incubated at 4° C. overnight in sealed container to let receptor to immobilize. Unbound receptor is washed away with 2 ml of 0.1% BSA/PBS. Then each well is filled with 250 µl of Blocking Buffer (2% nonfat dry milk in PBS) and blocked for 2–3 hours at room temperature. As a negative control, 3 wells with immobilized anti Fc-antibody are blocked with 2% nonfat milk in PBS. Fluorescently labeled peptide (SEQ ID NO: 4) is resolved in 0.1% BSA/PBS buffer, pH 8.5 and added at various concentrations (0 µM, 0.1 µM, 1 µM, 10 µM, 50 µM and 100 µM) into wells with immobilized Flt-1 receptor. To evaluate the receptor binding of chemically modified peptides (SEQ ID NO: 2, SEQ ID NO: 3), equal concentration of fluorescently labeled peptide and analyzed peptide are mixed and added into wells. To evaluate the ability to bind Flt-1 receptor for peptide SEQ ID NO:5 the fluorescein labeled peptide SEQ ID NO: 5 was added to immobilized receptor at concentration 50 µM. The specificity of ligand:receptor interaction is detected by inhibition of fluorescent labeled peptide binding to the receptor in the presence of free peptide (SEQ ID NO: 1). After 2 hours incubation, microtiter plates with bound peptide are washed 10 times with 0.1% BSA/PBS buffer, pH 8.5 and the fluorescence is measured using Microplate Fluorescence Reader FL600 (BioTek) ($\lambda_{ex}$=485 nm; $\lambda_{em}$=530 nm). Results are presented in. The binding of the peptide to the immobilized VEGF receptor-1 is concentration-dependent in comparison to control peptide. The analysis demonstrates that SEQ ID NO: 4 has high affinity binding for VEGF receptor-1 with a $K_d$ value of about 10 μM. 64% of the binding of fluorescent labeled peptide to immobilized VEGF receptor-1 was displaced by chemically modified peptide (SEQ ID NO: 3).

TABLE 5

| Analyzed compound | Concentration in μM | Fluorescence |
|---|---|---|
| SEQ ID NO: 4 | 0 | 0 |
| | 0.1 | 512 |
| | 1 | 932 |
| | 10 | 3375.5 |
| | 50 | 4675.5 |
| | 100 | 6706 |
| SEQ ID NO: 4 + SEQ ID NO: 1 | 50 50 | 3707.7 |
| SEQ ID NO: 4 + SEQ ID NO: 3 | 50 50 | 1683.2 |
| Control peptide | 0 | 0 |
| | 0.1 | 7 |
| | 1 | 20 |
| | 10 | 493 |
| | 100 | 1105 |
| SEQ ID NO: 5 | 50 | 5124.5 |

Example 15

The Ability of Conjugate NO.: 1 to interact with VEGF Receptor-1

The ability of Conjugate ID NO:1 to interact with VEGF receptor-1 was analyzed in receptor binding assay. Human Flt-1/Fc chimera was immobilized in microtiter plates as described in Example 14. Conjuguate ID NO 1 at various concentrations (0.3 nM; 0.9 nM; 2.8 nM; 8.4 nM; 25.25 nM; 75.75 nM; 227.3 nM; 681.8 nM) in 0.1% BSA/PBS, pH 7.5 was added into wells and incubated for 2 hours at room temperature. Unbound conjugate was washed with 0.1% BSA/PBS, pH 7.5 and the bound peroxidase activity was detected using ABTS/$H_2O_2$ reagent, as described above. Peroxidase conjugated with cysteine was used as control of specific binding. The data represent means from triplicate wells (Table 6). Peptide (SEQ ID NO: 4)-peroxidase conjugate demonstrated concentration-dependent specific binding to the VEGF receptor-1. The half-maximum binding concentration for conjugate NO.:1 (0.1 μM) was 50-fold higher than for peptide.

TABLE 6

| Analyzed compound | Concentration in nM | Receptor-bound Peroxidase activity, $A_{405}$ |
|---|---|---|
| Conjugate NO.: 1 | 0.312 | 0.019 |
| | 0.935 | 0.017 |
| | 2.8 | 0.031 |
| | 8.42 | 0.014 |
| | 25.25 | 0.092 |
| | 75.75 | 0.377 |
| | 227.3 | 0.941 |
| | 681.8 | 1.162 |
| Cys-Peroxidase conjugate (Control) | 227.3 | 0.022 |
| | 681.8 | 0.020 |

Example 16

Construction of the Phase Expressing SEQ ID NO: 1

The SEQ ID NO: 1 is expressed as fusion protein with minor coat protein III of E.coli bacteriophage M13. The phage vector fUSE5, containing Sfi I restriction sites in N-end of pIII was kindly provided by Dr. George Smith, University of Missouri, Columbia Mo. The DNA of fUSE5 (100 μg) vector was digested with Sfi I restrictase (Boehringer Mannheim Biochemica) at supplier recommended conditions, purified by phenol: chloroform extraction and isolated from 14-bp stuffer fragment by precipitation with isopropanol for 20 min on ice. The linearized vector contained two non-complementary Sfi I ends, can not be self ligated and allows oriented ligation of oligonucleotides with the appropriate cohesive ends. The oligonucleotide inserts coding SEQ ID NO: 1 and control peptides were synthesized by automatic solid phase oligonucleotide synthesis and purified by reverse phase chromatography. The sequences of oligonucleotides are represented in Sequence Listing. The 5'- and 3'-ends of oligonucleotide SEQ ID NO: 9; 10 and SEQ ID NO: 11 were annealed to two "half-site" fragments SEQ ID NO: 12 and SEQ ID NO: 13 to form cohesive termini complementary to Sfi I sites 1 and 2 in the vector.

Oligonucleotides were phosphorylated with T4 kinase, and annealed in 20 mM Tris-HCl, pH 7.5, 2 mM $MgCl_2$, 50 mM NaCl, by mixing 1.5 μg SEQ ID NO: 12, 1.2 μg SEQ ID NO: 13, and 0.5 μg SEQ ID NO: 9 (or other), heating to 65.degree. C. for 5 minutes and allowing the mixture to cool slowly to room temperature. This represented an approximate molar ratio of 5:100:100 (SEQ ID NO:9-SEQ ID NO:10: SEQ ID NO:11). The annealed oligonucleotide insert (200 ng) is then ligated to 20 μg of Sfi-I-cut fUSE5 RF DNA (molar ratio 1:5) to produce a double-stranded circular molecule with a small, single stranded gap. The annealed DNA was ligated in 20 mM Tris-HCl, pH 7.5, 5 mM MgCl.sub.2, 2 mM DTT, 1 mM ATP, by the addition of 20 units of T4 DNA ligase and incubated overnight at 15.degree. C. The ligated DNA was ethanol precipitated in the presence of 0.3M sodium acetate, resuspended in water and electro-transformed into competent E. coli MC1061 cells using a Gene Pulser electroporation apparatus (Bio Rad) at 1.8 kV/cm, 200Ω, 25 mF. After electroporation, E.coli cells were allowed to reparate at 37° C. for 1 hour in 2 ml of SOC medium (2% Bacto tryptone, 0.5% Bacto yeast extract, 10 mM NaCl, 2.5 mM KCl, 10 mM $MgCl_2$, 10 mM $MgSO_4$, 20 mM glucose, 0.2 mg/ml tetracycline) and plated on Petri dishes with Luria-Bertani (LB) agar, containing 100 mg/ml kanamycin and 40 mg/ml tetracycline. Plates were incubated overnight at 37° C. Phage from single colonies were amplified in LB medium and purified using double precipitation with polyethylene glycol, as described in Phage display of peptides and proteins, Ed. by B. Kay et al., Academic Press. San Diego, 1996. The structure of recombinant phage clones was confirmed by dideoxy DNA sequencing.

List of Oligonucleotide Sequences (1) SEQ ID NO: 9 (ONV5.2)
(A) LENGTH: 69 nucleotides
(B) TYPE: nucleotide

```
GG GCC GGT AAC GGG TAC GAG ATC GAG TGG TAC TCG TGG GTC ACG CAC

GGG ATG TAC GGT GGC GCT TCT G
```

Gln Gly Tyr Glu Ile Glu Trp Tyr Ser Trp Val Thr His Gly Met Tyr (SEQ ID NO:34)

(2) SEQ ID NO: 10 (ONV5.10)
(A) LENGTH: 69 nucleotides
(B) TYPE: nucleotide

```
GG GCC GGT CCG GAG CCC GAG GTC CGG TTG AGT CCG CCG GGT CAT ATC
CAG TCG CTC GGT GGC GCT TCT G
```

Pro Glu Pro Glu Val Arg Leu Ser Pro Pro Gly His Ile Gln Ser Leu (SEQ ID NO:35)

(3) SEQ ID NO: 11. (ONV40)
(A) LENGTH: 69 nucleotides
(B) TYPE: nucleotide

```
GG GCC GGT TTT GTG GGG GGG TGG TTG GTT CCG GAG GAC GAG CGG CTC
TAC CCG GAG GGT GGC GCT TCT G
```

Phe Val Gly Gly Trp Leu Val Pro Glu Asp Glu Arg Leu Tyr Pro Glu (SEQ ID NO:36)

(4) SEQ ID NO: 12 (ON 10)
(A) LENGTH: 10 nucleotides
(B) TYPE: nucleotide

```
AAGCGCCACC
```

(5) SEQ ID NO: 13 (ON 11)
(A) LENGTH: 11 nucleotides
(B) TYPE: nucleotide

```
ACCGGCCCCGT
```

Example 17

The Binding of SEQ ID NO: 1-Expressing Phase to VEGF Receptor-1

Binding assays with the SEQ ID NO: 1-expressing phage (V5.2) generated in Example 16 above were performed essentially as described by B. Kay et. al in Phage display of peptides and proteins, Academic Press, San Diego, 1996. Specifically, binding assays were performed in ninety-six-well breakaway streptavidin-coated microliter plates, preblocked with BSA (Boehringer Mannheim). Total binding capacity for biotin-labeled AB=1.5 µg/well. Immunoabsorbent assay plates were coated overnight at 4.degree. C. with 10 .mu.g/ml affinity-purified, biotin-labeled goat anti-human Fc IgG (ICN). Human Flt-1/Fc chimera (1 µg/200 µl in 0.1% BSA/PBS) was added into each well, and plate was incubated at 4° C. overnight in sealed container. Plates were blocked for 2 hours with 2% non-fat milk in PBS (Blocking Buffer). Phage suspensions diluted in Blocking Buffer to $10^9$ virions/200 µl were incubated for 30 min at room temperature. This step was necessary to block any non-specific protein-protein interactions that may occur between phages and surrounding proteins. After removal of the blocking buffer from microtiter plate, 100 µl of a phage suspension with or without competing compound was added to each well. The phage was allowed to bind immobilized receptor overnight at 4.degree. Three well for each phage clone were coated with anti-Fc antibody and used as control. Non-bound phage was removed by washing wells 10 times with 250 µl of PBS/0.05% Tween 20. Horseradish peroxidase conjugated mouse anti-M13 monoclonal antibody (Pharmacia/Biotech) was used to analyzed the binding. Peroxidase activity was detected by production a green color in the presence of ABTS/H2O2 reagent and quantified by reading the absorbance at 405 nm in plate reader FL600 (BioTek).

These results demonstrated that SEQ ID NO: 1 expressed as a fusion protein on the surface of phage particle retained the specific binding to the VEGF receptor-1 (Table 8.

TABLE 8

| N | PHAGE CLONE | ABSORBANCE, A 405 |
|---|---|---|
| 1 | V5.2 | 1.67 ± 0.09 |
| 2 | V5.10 | 0.039 ± 0.013 |
| 3 | V40 | 0.025 ± 0.014 |

Example 18

The Selectivity of SEQ ID NO:1-Expressing Phase to Human and Murine VEGF Receptor-1

The ability of SEQ ID NO: 1 selectively recognize the VEGF receptor-1 was examined using phage ELISA assay. Microtiter ELISA plates (Maxisorb, Nunc) were coated with human and rodent endothelial receptors (1 µg/well) in 100 µl of 50 mM $Na_2 CO_3$, pH 9.6 overnight at 4° C. Plates were blocked for 2 hours with 2% non-fat milk in PBS to prevent nonspecific binding. Then the SEQ ID NO: 1-expressing phage ($1\times10^9$ cfu/wel) was added to each well and allowed to bind immobilized receptors for 3 hours at 4.degree C. Non-bound phage was removed by repeated washings with PBS/0.05% Tween-20 and the amount of remain phage was determined with anti-M13 antibody as described above. The results of the binding assays employing the VEGF receptor-1 Flt-1 and the four other proteins are presented in Table 5. The SEQ ID NO: 1-expressing phage was highly selective to VEGF receptor-1, did not react with other human endothelial receptors, including VEGF receptor-2, which has 40% sequence homology with VEGF receptor-1. The cross-interaction of SEQ ID NO: 1 phage with murine VEGF receptor-1 was significant and selective.

TABLE 9

| No | Immobilized protein | Absorbance, A 405 |
|---|---|---|
| 1 | Human VEGF receptor-1/Flt-1 | 0.614 ± 0.005 |
| 2 | Human VEGF receptor-2/KDR | 0.085 ± 0.016 |
| 3 | Human sICAM-1 | 0.01 ± 0.029 |
| 4 | Anti-humanFc IgG | 0.051 ± 0.014 |
| 5 | Murine VEGF receptor-1/Flt-1 | 0.398 ± 0.006 |
| 6 | Murine VEGF receptor-2/Flk | 0.0097 ± 0.002 |
| 7 | Rat Neuropilin-1 | 0.278 ± 0.015 |

Example 19

The Binding of SEQ ID NO: 3-Polymer Conjugates to VEGF Receptor-1

The binding of SEQ ID NO: 3 conjugates with polymers (CON. NO.:2; CON. NO.:3; CON. NO.: 4), described in examples 3, 4 and 5, was analyzed using competitive receptor binding assay. The microtiter plates, coated with hrVEGF receptor-1 (1 μg/well) were prepared as described in Example 14. The SEQ ID NO: 1-expressing phage was used as competing agent. Phage suspension ($10^9$ cfu/ml) in 0.1% BSA/PBS was prepared and mixed with conjugates at various concentrations. The SEQ ID NO: 1-expressing phage along (Positive control) and mixture of phage with conjugates (200 μl/well) were added into microtiter ptates with immobilized receptor, incubated at room temperature for 4 hours. Non-bound phage was removed by washings wells 10 times with 250 μl of 0.1% BSA/PBS. The binding was detected using Recombinant Phage Detection Module (Pharmacia Biotech). Result of analysis are presented in Table 10.

TABLE 10

| No | Analyzed compound | Concentration, μM | % of inhibition |
|----|-------------------|-------------------|-----------------|
| 1 | Conjugate NO.: 2 | 50 | 28.76 |
| 2 | Conjugate NO.: 3 | 50 | 60.91 |
| 3 | Conjugate NO.: 4 | 0.1 | 7.32 |

Example 20

Inhibition of VEGF Binding to VEGF Receptor-1 by SEQ ID NO:1 Peptide and SEQ ID NO: 1-Expressing Phage The ability of SEQ ID NO:1 peptide and SEQ ID NO: 1-expressing phage to inhibit the vascular endothelial factor binding to the VEGF receptor-1 was analyzed using competitive receptor binding assay. Human VEGF receptor-1 coated plates were prepared as described in Example 11. Binding cocktails consisted of $5 \times 10^9$ cfu/ml SEQ ID NO:1-expressing phage or 30 μM of fluorescein labeled peptide (SEQ ID NO: 3); a various concentrations of human recombinant VEGF (R&D Systems), all within 0.1% BSA/PBS (Buffer B) for a final volume of 100 μl were assembled and added to wells with immobilized VEGF receptor-1 or anti-Fc antibody (Control). The cocktails were allowed to equilibrate for 4 hours at room temperature. After incubation, micrititer plates were washed with buffer B for 10 times. Fluorescein-labeled peptide (SEQ ID NO: 3) interaction with the receptor was detected by fluorescence reader as described in Example 11. SEQ ID NO:1-expressing phage binding to immobilized VEGF receptor-1 was analyzed by ELISA as described in Example 14. The binding was calculated in % to Positive control (VEGF receptor-1-bound phage or peptide in absence of competitor (VEGF)). The results are represented as average of triplicate measurement ±SD. As shown in Table 11, both SEQ ID NO: 3 peptide and SEQ ID NO: 1-expressing phage competed with VEGF for the high-affinity receptor binding. The half-maximum inhibition of SEQ ID NO: 3 peptide binding was detected in the presence of 5 nM VEGF.

TABLE 11

| VEGF concentration, nM | VEGFR1 bound phage, % | VEGFR1 bound peptide, % |
|---|---|---|
| 0 | 100 | 100 |
| 0.01 | 99.87 ± 0.69 | 96.21 ± 5.16 |
| 0.1 | 97.99 ± 3.77 | 79.34 ± 5.33 |
| 1 | 84.78 ± 0.63 | 61.44 ± 8.42 |
| 10 | 68.4 ± 2.55 | 40.8 ± 42 |
| 100 | 25.2 ± 1.24 | 15.41 ± 11.4 |

Example 21

SEQ ID NO:1-Expressing Phase Distribution in Tumor-Bearing Mice

Murine B16BL6 melanoma cells were cultured in D-MEM supplemented with 10% of FBS at 37° C. in humidified atmosphere with 5% CO2. The cells with a volume of 200 μl of PBS were implanted s.c. in female C57BL/6 mice. Two weeks after tumor implantation, the animals were injected i.v. with $1 \times 10^{10}$ virions of SEQ ID NO 1-expressing phage or control phage (random peptide phage library). The phage was allowed to circulate for 24 h and then animals were perfused through the heart with 10 ml of D-MEM medium. The tumor and organs from 3 mice per group were collected, weighted and homogenized. The phage titer in different organs was determined as described (Pasqualini R. et. al., Nature 380:364–366, 1996). The titer of recovered phage (cell transducting units per gram of tissue) from tumor, liver and brain is presented in Table 6. The 100-fold higher accumulation of the SEQ ID NO 1-expressing phage in the tumor compared to control phage was detected. The maximum accumulation of phage in mice injected with the ligand-expressing phage was determined in tumor (ratio tumor:liver=80.7). Control phage was more equally distributed in tumor and organs (ratio tumor:liver=4.29)

TABLE 12

| Organ | SEQ ID NO: 1-expressing phage CFU × $10^6$/g of tissue | Control phage CFU × $10^6$/g of tissue |
|---|---|---|
| Tumor | 26000 ± 926 | 368 ± 112 |
| Liver | 323 ± 14.9 | 85.8 ± 4.86 |
| Brain | 22.1 ± 9.6 | 7.68 ± 1.55 |

Example 22

Ability of Peptides to Inhibit the Endothelial Cell Proliferation

Endothelial cells, for example, human umbilical vein endothelial cells (HUVEC) which can be prepared or obtained commercially (Clonetics, San Diego, Calif.) are plated onto 96-well plates (Costar) at $10^4$ cells per well in 200 μl of EGM-2 medium (Clonetics) supplemented with 0.5% heat-inactivated fetal bovine serum. Cells are allowed to grow for 24 hours at 37° C. under 5% $CO_2$. Recombinant human VEGF is added to the wells (at 10 ng/ml final concentration) along or with the test compound (SEQ ID NO: 4) at various concentrations: 0 uM; 0.5 uM; 1 uM; 5 uM; 25 uM; 50 uM. Non-relevant peptide YAFGYPS (SEQ ID NO: 39) at the same concentration is used as control.

After 48 hours of incubation at 37° C. under 5% $CO_2$, 1 μgCi of [methyl-$^3$H]-thymidine (20 Ci/mmol; ICN) is added per well and plates are incubated for an additional 24 hours. The cells are then placed on ice, washed twice with EGM-2 medium containing 10% FBS and fixed for 10 minutes by adding 200 μl of ice-cold 10% trichloroacetic acid per well. After washing with ice-cold water, cells are lysed and DNA is solubilized in 50 μl of 2% SDS. [$^3$H]-Thymidine incorporation is determined by scintillation counting. Results are presented in Table 8 and expressed as the average of 3 different wells for each concentration of compound.

The results show the test compound inhibits endothelial cell proliferation with an IC.sub.50 of 5 μM. At higher concentration of the test compound the VEGF induced HUVEC proliferation was reduced by 70%.

TABLE 13

| Analyzed compound | Concentration in μM | VEGF-induced HUVEC proliferation in % to control |
|---|---|---|
| SEQ ID NO: 4 | 0 | 100 |
|  | 0.5 | 75 |
|  | 1 | 51 |
|  | 5 | 61 |
|  | 25 | 32 |
|  | 50 | 27 |
| Control peptide | 0 | 100 |
|  | 0.5 | 96.7 |
|  | 1 | 123.5 |
|  | 5 | 93.8 |
|  | 25 | 107.4 |
|  | 50 | 137 |

Example 23

Inhibition of Tumor-Induced Angiogenesis In Vivo by Peptides

For tumor-induced angiogenesis, the dorsal air sac-chamber was carried out in female C57BL/6 mice as described else (Itoh, T et al., *Cancer Res.*, 58: 1048–1051, 1998). Murine B16BL6 cell, a VEGF-producing melanoma, were washed three times and suspended in HBSS at a concentration of 5×10$^6$ cells/ml. A Millipore (Millipore Co., Redford, Mass.) was filed with 0.2 ml of either a cell suspension of HBSS and then implanted s.c. into the dorsal side of mice (day 0). Control mice were implanted with Millipore chambre along. The animals (5 mice per group) were treated s.c. with 20 mg/kg of the modified peptide (SEQ ID NO: 4) or the vehicle into 1 cm around the air sac. Treatments were performed daily from days 0 to 5.

To evaluate the antiangiogenic activity of the compounds, 7 days after tumor implantation, the animals were sacrificed and a wide rectangular incision was made in the skin of air sacs and photgraphed. The significant stimulation of angiogenesis was detected in mice implanted with B16BL6 melanoma cells. The treatment of animals with compound of this invention at dose 20 mg/kg/day inhibits tumor-induced angiogenesis to 70%.

Example 24

Alanine Substitution Mutations

The single point mutations in SEQ ID NO:1 insert coding sequence of the phage were produced as described previously (Hoess, R., Brinkmann, U., Handel, T., Pastan, I. *Gene*, 128: 43–49, 1993.). Briefly, a series of SEQ ID NO: 1 coding oligonucleotides in with a particular amino acid coding triplet was changed to GCT (alanine coding triplet) were synthesized. Mutated oligonucleotides were cloned in to fUSE5 phage vector as described in Example 16. All mutant phage clones were purified and verified by DNA sequencing.

The binding of mutated phage clones to immobilized Flt-1 receptor was analyzed by ELISA as described in Example 17.

TABLE 14

| Clone | Insert sequence | SEQ ID NO. | Binding to hFlt-1 in % |
|---|---|---|---|
| V5.2 | NGYEIEWYSWVTHGMY<br>(Asn-Gly-Tyr-Glu-Ile-Glu-Trp-Tyr-Ser-Trp-Val-Thr-His-Gly-Met-Tyr) | 1 | 100 |
| N1/A | AGYEIEWYSWVTHGMY<br>(Ala-Gly-Tyr-Glu-Ile-Glu-Trp-Tyr-Ser-Trp-Val-Thr-His-Gly-Met-Tyr) | 14 | 42.93 ± 25.76 |
| E4/A | NGYAIEWYSWVTHGMY<br>(Asn-Gly-Tyr-Ala-Ile-Glu-Trp-Tyr-Ser-Tr-Val-Thr-His-Gly-Met-Tyr) | 15 | 17.54 ± 5.31 |
| I5/A | NGYEAEWYSWVTHGMY<br>(Asn-Gly-Tyr-Glu-Ala-Glu-Trp-Tyr-Ser-Trp-Val-Thr-His-Gly-Met-Tyr) | 16 | 18.76 ± 0.26 |
| E6/A | NGYEIAWYSWVTHGMY<br>(Asn-Gly-Tyr-Glu-Ile-Ala-Trp-Tyr-Ser-Trp-Val-Thr-His-Gly-Met-Tyr) | 17 | 19.155 ± 14.07 |
| W7/A | NGYEIEAYSWVTHGMY<br>(Asn-Gly-Tyr-Glu-Ile-Glu-Ala-Tyr-Ser-Trp-Val-Thr-His-Gly-Met-Tyr) | 18 | 66.23 ± 27.07 |
| Y8/A | NGYEIEWASWVTHGMY<br>(Asn-Gly-Tyr-Glu-Ile-Glu-Trp-Ala-Ser-Trp-Val-Thr-His-Gly-Met-Tyr) | 19 | 67.035 ± 6.28 |
| S9/A | NGYEIEWYAWVTHGMY<br>(Asn-Gly-Tyr-Glu-Ile-Glu-Trp-Tyr-Ala-Trp-Val-Thr-His-Gly-Met-Tyr) | 20 | 101.69 ± 16.70 |
| W10/A | NGYEIEWYSAVTHGMY<br>(Asn-Gly-Tyr-Glu-Ile-Glu-Trp-Tyr-Ser-Ala-Val-Thr-His-Gly-Met-Tyr) | 21 | 22.08 ± 7.19 |

TABLE 14-continued

| Clone | Insert sequence | SEQ ID NO. | Binding to hFlt-1 in % |
|---|---|---|---|
| T12/A | NGYEIEWYSWVAHGMY<br>(Asn-Gly-Tyr-Glu-Ile-Glu-Trp-Tyr-Ser-Trp-Val-Ala-His-Gly-Met-Tyr) | 22 | 62.63 ± 22.58 |
| H13/A | NGYEIEWYSWVTAGMY<br>(Asn-Gly-Tyr-Glu-Ile-Glu-Trp-Tyr-Ser-Trp-Val-Thr-Ala-Gly-Met-Tyr) | 23 | 55.34 ± 10.78 |
| M15/A | NGYEIEWYSWVTHGAY<br>(Asn-Gly-Tyr-Glu-Ile-Glu-Trp-Tyr-Ser-Trp-Val-Thr-His-Gly-Ala-Tyr) | 24 | 78.24 ± 19.42 |
| Y16/A | NGYEIEWYSWVTHGMA<br>(Asn-Gly-Tyr-Glu-Ile-Glu-Trp-Tyr-Ser-Trp-Val-Thr-His-Gly-Met-Ala) | 25 | 15.30 ± 15.27 |
| E46/A | NGYAIAWYSWVTHGMY<br>(Asn-Gly-Tyr-Ala-Ile-Ala-Trp-Tyr-Ser-Trp-Val-Thr-His-Gly-Met-Tyr) | 26 | 44.46 ± 7.05 |
| W710/A | NGYEIEAYSAVTHGMY<br>(Asn-Gly-Tyr-Glu-Ile-Glu-Ala-Tyr-Ser-Ala-Val-Thr-His-Gly-Met-Tyr) | 27 | 62.15 ± 22.16 |
| V5.2/1 | EIEWYSW<br>(Glu-Ile-Glu-Trp-Tyr-Ser-Trp) | 28 | 6.55 ± 15.81 |
| V5.2/5 | EIEWYSWVTHGMY<br>(Glu-Ile-Glu-Trp-Tyr-Ser-Trp-Val-Thr-His-Gly-Met-Tyr) | 29 | 85.6 ± 22.61 |

Example 25

Association of SEQ ID NO: 1 with Erythropoietin.

The murine erythropoietin (mEPO) gene was cloned in pcDNA/Amp1.1 expression vector using RT/PCR. CDNA encoded mEPO was obtained by reverse transcription of mRNA extracted from kidneys of mice treated for 3 days with phenylhydrazine (Shoemaker C B., et al., Mol. Cel. Biol.,1986). Amplification of DNA was performed using the sense 5'-ATAACAAGCTTGGCGCGGAGATGGGGGTG SEQ ID NO: 30 and antisense 5'ATAACTCTAGAACG-GTGGCAGCAGCATGTCAC SEQ ID NO: 31 primers. The amplified mEPO gene was inserted into the XbaI and Hind III sites of pcDNA/Amp1.1, and sequence was confirmed by DNA sequencing. Cos-7 cells were transfected with pCMV/EPO plasmide, and expression of recombinant mEPO was evaluated by Quantikine IVD Erythropoietin ELISA kit. The physiological activity of recombinant mEPO was evaluated in vivo by measured of hematocrit.

Synthetic oligonucleotide encoded peptide SEQ ID NO: 1 flanked with restriction sites and SerGlyAlaGly linker (SEQ ID NO: 41) was synthesized (5'ACAACTCTAGAATGAACGGGTACGAGATCGAGTGGTACTCGTGGGTCACGCACGGG

ATGTACTCTGGGGCCGGATCTAGACAACA SEQ ID NO: 32).

Double strand DNA fragment was synthesized by using DNA extension reaction and short complementary oligo. Further, the SEQ ID NO:1 encoding DNA was restricted by Xba I and cloned in open reading frame of mEPO into pCMV/EPO vector. Structure of SEQ ID NO:1-EPO fusion protein was confirmed by DNA sequencing.

Example 26

Construction of Adenoviral Vectors Encoding SEQ ID NO:1

This example describes the construction of adenoviral vectors encoding fiber sequences having insertions of SEQ ID NO:1 peptide in a loop of the knob region of the adenovirus fiber protein.

The transfer plasmid p193 F5F2K(SP5.2) was employed to obtain the corresponding adenoviral vectors comprising the SEQ ID NO: 1 peptide. This was accomplished by digesting these plasmids (which contain the essential E4 region of adenovirus) with Sal I, and transfecting them into 293 cells that already had been infected 1 hour earlier with the adenovirus vector AdZ.E4Gus. This adenovirus vector lacks the E4 region and cannot replicate in 293 cells without the E4 genes. Only when AdZ.E4Gus DNA recombines with plasmid DNA such as p193 F5F2K, p193 F5F2K(SP5.2) to obtain the E4 genes is the vector able to replicate in 293 cells. During this recombination to rescue the adenoviral vector, the newly formed vector also picks up the mutated fiber sequence encoded by the plasmids.

Viable recombinant E4.sup.+adenovirus containing the F2K(SP5.2) DNA sequence (i.e., AdZ.SP5.2) was isolated by plaquing the transfected cell lysates 5 days after transfection. The recombinant adenoviruses were then plaque-purified 2 times on 293 cells. The purified plaques were amplified on 293 cells. All viruses were purified from infected cells at 2 days post-infection by 3 freeze-thaw cycles followed by two successive bandings on CsCl gradients. Purified virus was dialyzed into 10 mM Tris, 150 mM NaCl, pH 7.8, containing 10 mM $MgCl_2$, 3% sucrose, and was frozen at −80 degree. until required for use. The purified viruses were verified by PCR to contain SEQ ID NO: 1 encoding insert.

All publications or patents cited in this application are herein incorporated by references.

We claim:

1. A compound comprising amino acid sequence Glu-Ile-Glu-Trp-Tyr-Ser-Trp-Val-Thr-His-Gly-Met-Tyr (SEQ ID NO:29).

2. A pharmaceutical composition comprising the compound of claim 1 and a biological agent.

3. A pharmaceutical composition comprising the compound of claim 1 and a carrier.

4. The compound of claim 1, wherein the compound further comprises a biological agent conjugated thereto.

5. The compound of claim 4, wherein said biological agent comprises a prodrug.

6. The compound of claim 4, wherein said biological agent is a therapeutic agent.

* * * * *

SEQUENCE LISTING

<160> NUMBER OF SEQ ID NOS: 33

<210> SEQ ID NO 1
<211> LENGTH: 16
<212> TYPE: PRT
<213> ORGANISM: Artificial Sequence
<220> FEATURE:
<223> OTHER INFORMATION: Chemical peptide synthesis and biosynthesis
      utilizing E. coli
<220> FEATURE:
<221> NAME/KEY: MOD_RES
<222> LOCATION: (16)..(16)
<223> OTHER INFORMATION: AMIDATION

<400> SEQUENCE: 1

Asn Gly Tyr Glu Ile Glu Trp Tyr Ser Trp Val Thr His Gly Met Tyr
1               5                   10                  15

<210> SEQ ID NO 2
<211> LENGTH: 17
<212> TYPE: PRT
<213> ORGANISM: Artificial Sequence
<220> FEATURE:
<223> OTHER INFORMATION: Chemical peptide synthesis and biosynthesis
      utilizing E. coli
<220> FEATURE:
<221> NAME/KEY: MOD_RES
<222> LOCATION: (17)..(17)
<223> OTHER INFORMATION: AMIDATION

<400> SEQUENCE: 2

Cys Asn Gly Tyr Glu Ile Glu Trp Tyr Ser Trp Val Thr His Gly Met
1               5                   10                  15

Tyr

<210> SEQ ID NO 3
<211> LENGTH: 17
<212> TYPE: PRT
<213> ORGANISM: Artificial Sequence
<220> FEATURE:
<223> OTHER INFORMATION: Chemical peptide synthesis and biosynthesis
      utilizing E. coli
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (17)..(17)
<223> OTHER INFORMATION: AMIDATION

<400> SEQUENCE: 3

Cys Asn Gly Tyr Glu Ile Glu Trp Tyr Ser Trp Val Thr His Gly Met
1               5                   10                  15

Tyr

<210> SEQ ID NO 4
<211> LENGTH: 16
<212> TYPE: PRT
<213> ORGANISM: Artificial Sequence
<220> FEATURE:
<223> OTHER INFORMATION: Chemical peptide synthesis and biosynthesis
      utilizing E. coli
<220> FEATURE:
<221> NAME/KEY: MOD_RES
<222> LOCATION: (1)..(1)
<223> OTHER INFORMATION: Fluorescein 5 carbonyl
<220> FEATURE:

```
<221> NAME/KEY: MOD_RES
<222> LOCATION: (16)..(16)
<223> OTHER INFORMATION: AMIDATION

<400> SEQUENCE: 4

Asn Gly Tyr Glu Ile Glu Trp Tyr Ser Trp Val Thr His Gly Met Tyr
1               5                   10                  15

<210> SEQ ID NO 5
<211> LENGTH: 19
<212> TYPE: PRT
<213> ORGANISM: Artificial Sequence
<220> FEATURE:
<223> OTHER INFORMATION: Chemical peptide synthesis and biosynthesis
      utilizing E. coli
<220> FEATURE:
<221> NAME/KEY: MOD_RES
<222> LOCATION: (1)..(1)
<223> OTHER INFORMATION: Fluorescein-5-carbonyl
<220> FEATURE:
<221> NAME/KEY: MOD_RES
<222> LOCATION: (19)..(19)
<223> OTHER INFORMATION: AMIDATION

<400> SEQUENCE: 5

Glu Glu Glu Asn Gly Tyr Glu Ile Glu Trp Tyr Ser Trp Val Thr His
1               5                   10                  15

Gly Met Tyr

<210> SEQ ID NO 6
<211> LENGTH: 15
<212> TYPE: PRT
<213> ORGANISM: Artificial Sequence
<220> FEATURE:
<223> OTHER INFORMATION: Chemical peptide synthesis and biosynthesis
      utilizing E. coli
<220> FEATURE:
<221> NAME/KEY: MOD_RES
<222> LOCATION: (1)..(1)
<223> OTHER INFORMATION: Fluorescein-5-carbonyl
<220> FEATURE:
<221> NAME/KEY: MOD_RES
<222> LOCATION: (15)..(15)
<223> OTHER INFORMATION: AMIDATION

<400> SEQUENCE: 6

Asn Gly Tyr Ile Glu Trp Tyr Ser Trp Val Thr His Gly Met Tyr
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Chemical peptide synthesis and biosynthesis
      utilizing E. coli
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (7)..(9)
<223> OTHER INFORMATION: Xaa = any amino acid
<220> FEATURE:
<221> NAME/KEY: MISC_FEATURE
<222> LOCATION: (11)..(15)
<223> OTHER INFORMATION: Xaa = any amino acid

<400> SEQUENCE: 7

Asn Xaa Xaa Glu Ile Glu Xaa Xaa Xaa Trp Xaa Xaa Xaa Xaa Xaa Tyr
```

<210> SEQ ID NO 8
<211> LENGTH: 16
<212> TYPE: PRT
<213> ORGANISM: Artificial Sequence
<220> FEATURE:
<223> OTHER INFORMATION: Chemical peptide synthesis and biosynthesis utilizing E. coli
<220> FEATURE:
<221> NAME/KEY: MISC_FEATURE
<222> LOCATION: (1)..(1)
<223> OTHER INFORMATION: Xaa = Asn or Gln
<220> FEATURE:
<221> NAME/KEY: MISC_FEATURE
<222> LOCATION: (2)..(3)
<223> OTHER INFORMATION: Xaa = Any amino acid
<220> FEATURE:
<221> NAME/KEY: MISC_FEATURE
<222> LOCATION: (4)..(4)
<223> OTHER INFORMATION: Xaa = Glu or Asp
<220> FEATURE:
<221> NAME/KEY: MISC_FEATURE
<222> LOCATION: (5)..(5)
<223> OTHER INFORMATION: Xaa = Ile, Leu, Val, or Met
<220> FEATURE:
<221> NAME/KEY: MISC_FEATURE
<222> LOCATION: (6)..(6)
<223> OTHER INFORMATION: Xaa = Glu or Asp
<220> FEATURE:
<221> NAME/KEY: MISC_FEATURE
<222> LOCATION: (7)..(9)
<223> OTHER INFORMATION: Xaa = Any amino acid
<220> FEATURE:
<221> NAME/KEY: MISC_FEATURE
<222> LOCATION: (10)..(10)
<223> OTHER INFORMATION: Xaa = Trp, Phe, Tyr, or His
<220> FEATURE:
<221> NAME/KEY: MISC_FEATURE
<222> LOCATION: (11)..(15)
<223> OTHER INFORMATION: Xaa = Any amino acid
<220> FEATURE:
<221> NAME/KEY: MISC_FEATURE
<222> LOCATION: (16)..(16)
<223> OTHER INFORMATION: Xaa = Trp, Phe, Tyr, or His

<400> SEQUENCE: 8

Xaa Xaa Xaa Xaa Xaa Xaa Xaa Xaa Xaa Xaa Xaa Xaa Xaa Xaa Xaa Xaa
 1               5                  10                  15

<210> SEQ ID NO 9
<211> LENGTH: 69
<212> TYPE: DNA
<213> ORGANISM: Artificial Sequence
<220> FEATURE:
<223> OTHER INFORMATION: Synthetic DNA

<400> SEQUENCE: 9
gggccggtaa cgggtacgag atcgagtggt actcgtgggt cacgcacggg atgtacggtg    60
gcgcttctg                                                            69

<210> SEQ ID NO 10
<211> LENGTH: 69
<212> TYPE: DNA
<213> ORGANISM: Artificial Sequence
<220> FEATURE:
<223> OTHER INFORMATION: Synthetic DNA

<400> SEQUENCE: 10
gggccggtcc ggagcccgag gtccggttga gtccgccggg tcatatccag tcgctcggtg    60
gcgcttctg                                                            69

<210> SEQ ID NO 11
<211> LENGTH: 69
<212> TYPE: DNA
<213> ORGANISM: Artificial Sequence
<220> FEATURE:
<223> OTHER INFORMATION: Synthetic DNA

<400> SEQUENCE: 11
gggccggttt tgtgggggggg tggttggttc cggaggacga gcggctctac ccggagggtg    60
gcgcttctg                                                             69

<210> SEQ ID NO 12
<211> LENGTH: 10
<212> TYPE: DNA
<213> ORGANISM: Artificial Sequence
<220> FEATURE:
<223> OTHER INFORMATION: Synthetic DNA

<400> SEQUENCE: 12
aagcgccacc                                                            10

<210> SEQ ID NO 13
<211> LENGTH: 11
<212> TYPE: DNA
<213> ORGANISM: Artificial Sequence
<220> FEATURE:
<223> OTHER INFORMATION: Synthetic DNA

<400> SEQUENCE: 13
accggccccg t                                                          11

<210> SEQ ID NO 14
<211> LENGTH: 16
<212> TYPE: PRT
<213> ORGANISM: Artificial Sequence
<220> FEATURE:
<223> OTHER INFORMATION: Chemical peptide synthesis and biosynthesis
      utilizing E. coli

<400> SEQUENCE: 14

Ala Gly Tyr Glu Ile Glu Trp Tyr Ser Trp Val Thr His Gly Met Tyr
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Chemical peptide synthesis and biosynthesis
      utilizing E. coli

<400> SEQUENCE: 15

Asn Gly Tyr Ala Ile Glu Trp Tyr Ser Trp Val Thr His Gly Met Tyr
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Chemical peptide synthesis and biosynthesis
      utilizing E. coli

<400> SEQUENCE: 16

Asn Gly Tyr Glu Ala Glu Trp Tyr Ser Trp Val Thr His Gly Met Tyr

```
<210> SEQ ID NO 17
<211> LENGTH: 16
<212> TYPE: PRT
<213> ORGANISM: Artificial Sequence
<220> FEATURE:
<223> OTHER INFORMATION: Chemical peptide synthesis and biosynthesis
      utilizing E. coli

<400> SEQUENCE: 17

Asn Gly Tyr Glu Ile Ala Trp Tyr Ser Trp Val Thr His Gly Met Tyr
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Chemical peptide synthesis and biosynthesis
      utilizing E. coli

<400> SEQUENCE: 18

Asn Gly Tyr Glu Ile Glu Ala Tyr Ser Trp Val Thr His Gly Met Tyr
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Chemical peptide synthesis and biosynthesis
      utilizing E. coli

<400> SEQUENCE: 19

Asn Gly Tyr Glu Ile Glu Trp Ala Ser Trp Val Thr His Gly Met Tyr
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Chemical peptide synthesis and biosynthesis
      utilizing E. coli

<400> SEQUENCE: 20

Asn Gly Tyr Glu Ile Glu Trp Tyr Ala Trp Val Thr His Gly Met Tyr
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Chemical peptide synthesis and biosynthesis
      utilizing E. coli

<400> SEQUENCE: 21

Asn Gly Tyr Glu Ile Glu Trp Tyr Ser Ala Val Thr His Gly Met Tyr
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Chemical peptide synthesis and biosynthesis
```

-continued utilizing E. coli

<400> SEQUENCE: 22

Asn Gly Tyr Glu Ile Glu Trp Tyr Ser Trp Val Ala His Gly Met Tyr
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Chemical peptide synthesis and biosynthesis
      utilizing E. coli

<400> SEQUENCE: 23

Asn Gly Tyr Glu Ile Glu Trp Tyr Ser Trp Val Thr Ala Gly Met Tyr
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Chemical peptide synthesis and biosynthesis
      utilizing E. coli

<400> SEQUENCE: 24

Asn Gly Tyr Glu Ile Glu Trp Tyr Ser Trp Val Thr His Gly Ala Tyr
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Chemical peptide synthesis and biosynthesis
      utilizing E. coli

<400> SEQUENCE: 25

Asn Gly Tyr Glu Ile Glu Trp Tyr Ser Trp Val Thr His Gly Met Ala
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Chemical peptide synthesis and biosynthesis
      utilizing E. coli

<400> SEQUENCE: 26

Asn Gly Tyr Ala Ile Ala Trp Tyr Ser Trp Val Thr His Gly Met Tyr
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Chemical peptide synthesis and biosynthesis
      utilizing E. coli

<400> SEQUENCE: 27

Asn Gly Tyr Glu Ile Glu Ala Tyr Ser Ala Val Thr His Gly Met Tyr
1               5                   10                  15

<210> SEQ ID NO 28

```
<211> LENGTH: 7
<212> TYPE: PRT
<213> ORGANISM: Artificial Sequence
<220> FEATURE:
<223> OTHER INFORMATION: Chemical peptide synthesis and biosynthesis
      utilizing E. coli

<400> SEQUENCE: 28

Glu Ile Glu Trp Tyr Ser Trp
1               5

<210> SEQ ID NO 29
<211> LENGTH: 13
<212> TYPE: PRT
<213> ORGANISM: Artificial Sequence
<220> FEATURE:
<223> OTHER INFORMATION: Chemical peptide synthesis and biosynthesis
      utilizing E. coli

<400> SEQUENCE: 29

Glu Ile Glu Trp Tyr Ser Trp Val Thr His Gly Met Tyr
1               5                   10

<210> SEQ ID NO 30
<211> LENGTH: 29
<212> TYPE: DNA
<213> ORGANISM: Artificial Sequence
<220> FEATURE:
<223> OTHER INFORMATION: Synthetic DNA

<400> SEQUENCE: 30
ataacaagct tggcgcggag atgggggtg                                         29

<210> SEQ ID NO 31
<211> LENGTH: 32
<212> TYPE: DNA
<213> ORGANISM: Artificial Sequence
<220> FEATURE:
<223> OTHER INFORMATION: Synthetic DNA

<400> SEQUENCE: 31
ataactctag aacggtggca gcagcatgtc ac                                     32

<210> SEQ ID NO 32
<211> LENGTH: 85
<212> TYPE: DNA
<213> ORGANISM: Artificial Sequence
<220> FEATURE:
<223> OTHER INFORMATION: Synthetic DNA

<400> SEQUENCE: 32
acaactctag aatgaacggg tacgagatcg agtggtactc gtgggtcacg cacgggatgt       60
actctggggc cggatctaga caaca                                             85

<210> SEQ ID NO 33
<211> LENGTH: 13
<212> TYPE: DNA
<213> ORGANISM: Artificial Sequence
<220> FEATURE:
<223> OTHER INFORMATION: Synthetic DNA

<400> SEQUENCE: 33
gccgccacca tgg                                                          13
```